United States Patent
Petri, Jr. et al.

(10) Patent No.: US 10,046,030 B2
(45) Date of Patent: Aug. 14, 2018

(54) COMPOSITIONS AND METHODS FOR PREVENTING AND TREATING INFECTION

(71) Applicant: University of Virginia Patent Foundation, Charlottesville, VA (US)

(72) Inventors: William A. Petri, Jr., Charlottesville, VA (US); Erica Buonomo, Malden, MA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/517,191

(22) PCT Filed: Oct. 7, 2015

(86) PCT No.: PCT/US2015/054498
§ 371 (c)(1),
(2) Date: Apr. 6, 2017

(87) PCT Pub. No.: WO2016/057671
PCT Pub. Date: Apr. 14, 2016

(65) Prior Publication Data
US 2017/0368143 A1 Dec. 28, 2017

Related U.S. Application Data

(60) Provisional application No. 62/146,579, filed on Apr. 13, 2015, provisional application No. 62/060,725, filed on Oct. 7, 2014.

(51) Int. Cl.
| | |
|---|---|
| *A61K 38/20* | (2006.01) |
| *C07K 14/54* | (2006.01) |
| *A61K 45/06* | (2006.01) |
| *A61K 31/4164* | (2006.01) |
| *A61K 31/733* | (2006.01) |
| *A61K 35/747* | (2015.01) |
| *G01N 33/50* | (2006.01) |
| *A61K 35/00* | (2006.01) |

(52) U.S. Cl.
CPC .......... *A61K 38/20* (2013.01); *A61K 31/4164* (2013.01); *A61K 31/733* (2013.01); *A61K 35/747* (2013.01); *A61K 45/06* (2013.01); *G01N 33/5047* (2013.01); *A61K 2035/115* (2013.01); *C07K 14/54* (2013.01)

(58) Field of Classification Search
None
See application file for complete search history.

(56) References Cited

FOREIGN PATENT DOCUMENTS

WO WO2014121301 8/2014

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Bolla et al., "Protective effect of a mixture of kefir-isolated lactic acid bacteria and yeasts in a hamster model of Clostridium difficile infection", Anaerobe, (2013), vol. 21, 28-33.
Zaph C. et al. "Commensal-dependent expression of IL-25 regulates the IL-23-IL-17 axis in the intestine", Journal of Exp. Medicine, 2008, V. 205, No. 10, 2991-2198.
Fort, M., et al., "IL-25 Induces IL-4, IL-5, and IL-13 and TH2-Associated Pathologies In Vivo", Immunity, vol. 15, 985-995, 2001.
Spencer, L., et al., "Human eosinophils constitutively express multiple Th1, Th2, and immunoregulatory cytokines that are secreted rapidly and differentially", Jrnl. of Leukocyte Biology, V. 85, 2009, 117-123.
Cowardin, C., et al., "Inflammasome Activation Contributes to Interleukin-23 Production in Response to Clostridium difficile", MBio, 2015, vol. 6 (1), 1-9.
Buonomo, E., et al., "Role of Interleukin 23 Signaling in Clostridium difficile Colitis", Jrnl. of Infect. Dis., 2013, 917-920.
Zaiss M. et al. "IL-1B Suppresses Innate IL-25 and IL-33 Production and Maintains Helminth Chronicity", PLOS Pathogens, V9, 18, e1003531, 2013.
Hasegawa, M., et al., "Protective Role of Commensals against Clostridium difficile Infection via an IL-1B-Mediated Positive-Feedback Loop", Jrnl. of Immunology, 2012, 189, 3085-3091.
Buonomo, E, et al., "Microbiota-Regulated IL-25 Increases Eosinophil Number To Provide Protection during Clostridium difficile Infection", Cell Reports 16, 432-443, 2016.
Buonomo, E., et al., "The microbiota and immune response during Clostridium difficile infection", Anaerobe 41 (2016), 79-84.

* cited by examiner

*Primary Examiner* — Bridget E Bunner
*Assistant Examiner* — Fozia Hamud
(74) *Attorney, Agent, or Firm* — Rodney L. Sparks

(57) ABSTRACT

The present invention encompasses compositions and methods useful to treat or prevent *Clostridium difficile* antibiotic-associated colitis through administration of IL-25 and/or downstream cytokines IL-13, IL-4, and IL-5. It is disclosed herein that IL-25 expression is decreased during antibiotic treatment and during bacterial infection and that treatment with IL-25 protein is protective during infection. It is further disclosed herein the unexpected result that IL-25 treatment protects against *C. difficile*-associated mortality and morbidity. The present application further describes an unexpected result regarding eosinophils and their role in combating infection and their relationship to the effectiveness of IL-25.

31 Claims, 44 Drawing Sheets

FIG. 1: IL-25 is protective during *Clostridium difficile* infection.

FIG. 2: IL-25 expression is decreased with antibiotics and throughout the course of infection when compared with untreated controls.

FIG. 3: IL-25 administration is associated with increased eosinophil recruitment to the lamina propria on Day 3 of infection.

FIG 4: IL-25 induces IL-4 production from eosinophils in the lamina propria on Day 3 of infection.

FIG 5: Anti-inflammatory(IL-10) responses are increased in cecal tissue with IL-25 treatment during infection.

FIG 6: Mucin (MUC2) is enhanced in cecal tissue with IL-25 treatment during infection.

How does IL-25 skew the immune response in the absence of CDI
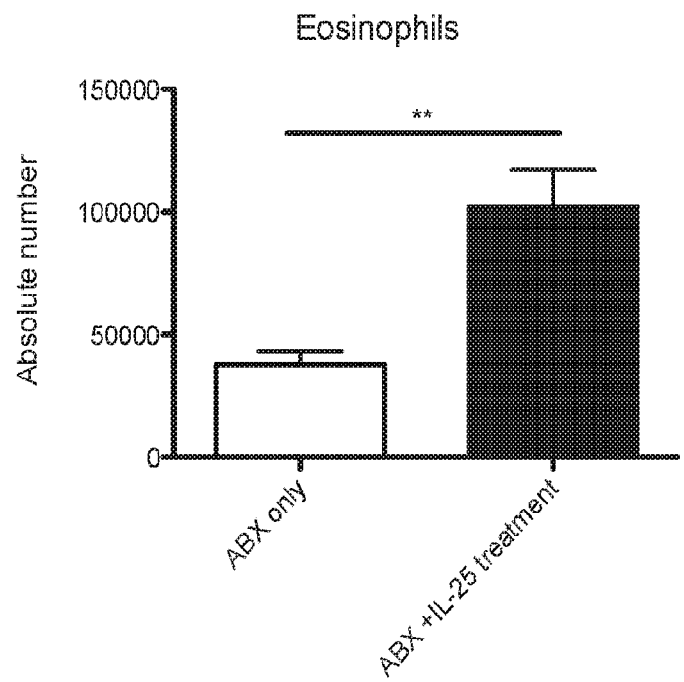
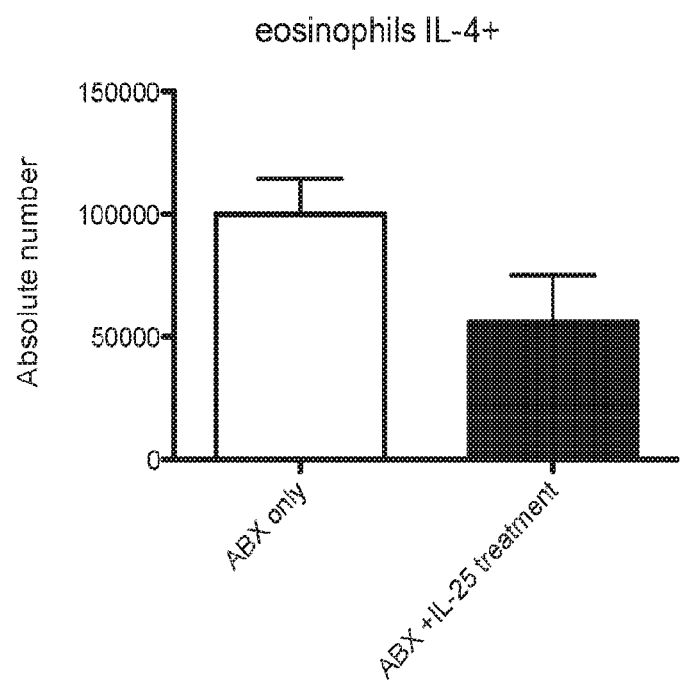
FIG. 11

Eosinophils are not protective in the absence of IL-25

Recombinant IL-25 Protein Assay

Restoration of IL-25 signaling prior to infection protects mice from morbidity and mortality IL-25 signaling protects against epithelial disruption but does not alter *C. difficle* burden

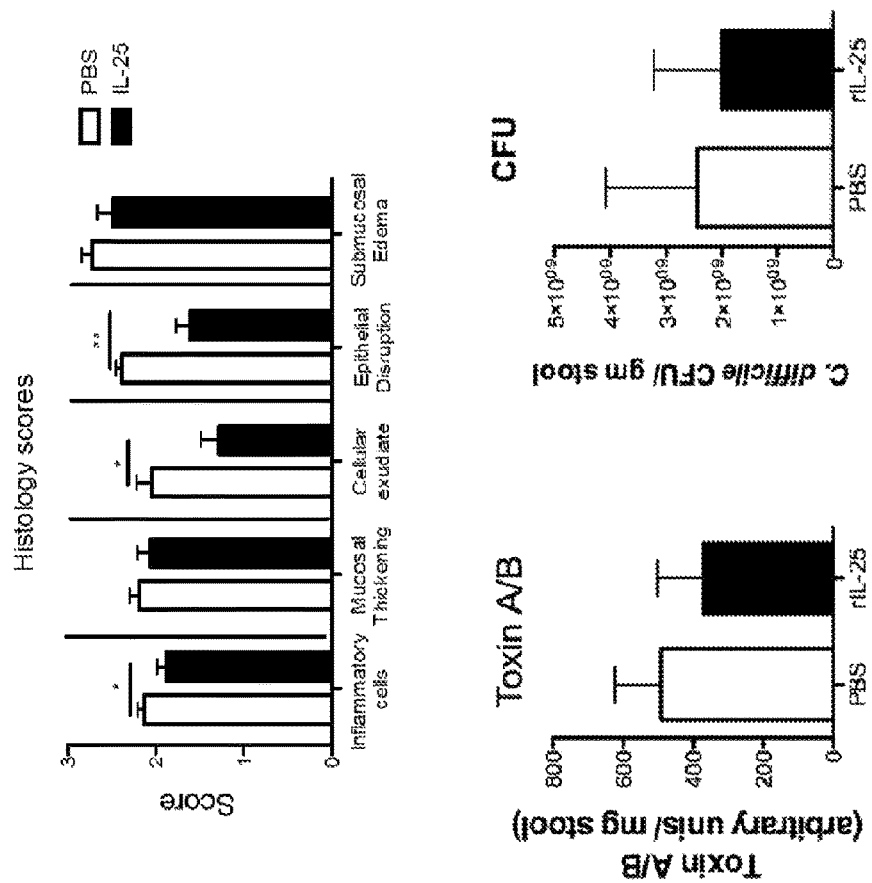
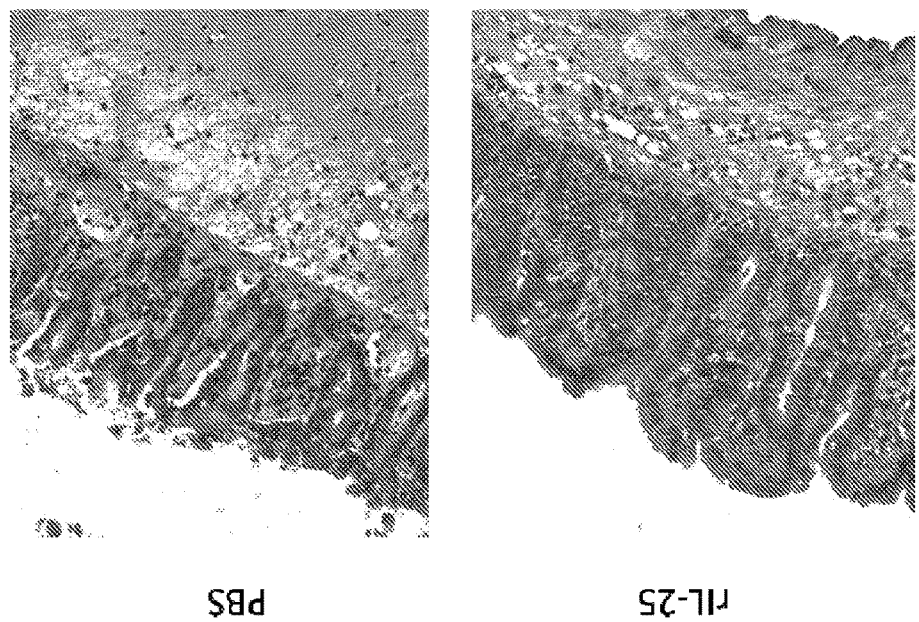
FIG. 18

Eosinophil depletion negates the ability of IL-25 to decrease bacterial translocation to the liver

- IL-25 is downregulated during human and murine CDI.
- Repletion of IL-25 is protective against CDI-associated mortality.
- IL-25 induces IL-4 production from recruited eosinophils.
- Eosinophils are necessary for IL-25 dependent protection.
- IL-25/eosinophilia may protect via physical barriers and/or by its ability to inhibit bacterial translocation to the gut.

IL-25 does not require adaptive immunity to protect against *C. Difficile*

Eosinophils may provide protection by controlling commensal translocation

B.

SEQUENCE LISTING

<160> NUMBER OF SEQ ID NOS: 2

<210> SEQ ID NO 1
<211> LENGTH: 177
<212> TYPE: PRT
<213> ORGANISM: Homo sapiens

<400> SEQUENCE: 1

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser

-continued

```
                35                  40                  45
Glu Glu Leu Leu Arg Trp Ser Thr Val Pro Val Pro Pro Leu Glu Pro
             50                  55                  60
Ala Arg Pro Asn Arg His Pro Glu Ser Cys Arg Ala Ser Glu Asp Gly
 65                  70                  75                  80
Pro Leu Asn Ser Arg Ala Ile Ser Pro Trp Arg Tyr Glu Leu Asp Arg
                 85                  90                  95
Asp Leu Asn Arg Leu Pro Gln Asp Leu Tyr His Ala Arg Cys Leu Cys
                100                 105                 110
Pro His Cys Val Ser Leu Gln Thr Gly Ser His Met Asp Pro Arg Gly
                115                 120                 125
Asn Ser Glu Leu Leu Tyr His Asn Gln Thr Val Phe Tyr Arg Arg Pro
                130                 135                 140
Cys His Gly Glu Lys Gly Thr His Lys Gly Tyr Cys Leu Glu Arg Arg
145                 150                 155                 160
Leu Tyr Arg Val Ser Leu Ala Cys Val Cys Val Arg Pro Arg Val Met
                165                 170                 175
Gly
```

<210> SEQ ID NO 2
<211> LENGTH: 161
<212> TYPE: PRT
<213> ORGANISM: Homo sapiens

<400> SEQUENCE: 2

```
Met Tyr Gln Val Val Ala Phe Leu Ala Met Val Met Gly Thr His Thr
  1               5                  10                  15
Tyr Ser His Trp Pro Ser Cys Cys Pro Ser Lys Gly Gln Asp Thr Ser
                 20                  25                  30
Glu Glu Leu Leu Arg Trp Ser Thr Val Pro Val Pro Pro Leu Glu Pro
             35                  40                  45
Ala Arg Pro Asn Arg His Pro Glu Ser Cys Arg Ala Ser Glu Asp Gly
 50                  55                  60
Pro Leu Asn Ser Arg Ala Ile Ser Pro Trp Arg Tyr Glu Leu Asp Arg
 65                  70                  75                  80
Asp Leu Asn Arg Leu Pro Gln Asp Leu Tyr His Ala Arg Cys Leu Cys
                 85                  90                  95
Pro His Cys Val Ser Leu Gln Thr Gly Ser His Met Asp Pro Arg Gly
                100                 105                 110
Asn Ser Glu Leu Leu Tyr His Asn Gln Thr Val Phe Tyr Arg Arg Pro
                115                 120                 125
Cys His Gly Glu Lys Gly Thr His Lys Gly Tyr Cys Leu Glu Arg Arg
                130                 135                 140
Leu Tyr Arg Val Ser Leu Ala Cys Val Cys Val Arg Pro Arg Val Met
145                 150                 155                 160
Gly
```

COMPOSITIONS AND METHODS FOR PREVENTING AND TREATING INFECTION

CROSS REFERENCE TO RELATED APPLICATIONS

This application is a national stage filing of International Application No. PCT/US2015/054498, filed Oct. 7, 2015, which claims priority under 35 U.S.C. § 119(e) to U.S. Provisional Application Ser. No. 62/060,725 filed Oct. 7, 2014 and U.S. Provisional Application Ser. No. 62/146,579 filed Apr. 13, 2015, the disclosures of which are incorporated by reference in their entirety herein.

STATEMENT REGARDING FEDERALLY SPONSORED RESEARCH OR DEVELOPMENT

This invention was made with government support under Grant No. AI026649, awarded by The National Institutes of Health. The government has certain rights in the invention.

BACKGROUND

*Clostridium difficile* is a gram-positive, spore-forming anaerobe that infects the gut when the natural flora has been disrupted, primarily through antibiotic treatment. It is currently the leading cause of nosocomial infections in the United States, resulting in approximately 14,000 deaths per year and costing the US health care system an estimated $4.8 billion annually.[1-6] Disease can range from asymptomatic colonization, to mild diarrhea, to life threatening pseudomembranous colitis and toxic megacolon. A hypervirulent strain of *C. difficile* is the cause of 30-day mortality in up to 15% of patients diagnosed with *C. difficile* infection (CDI).[2] Current therapy involves removal of the offending antibiotic and starting vancomycin or metronidazole treatment, which can inhibit the reestablishment of beneficial endogenous flora while fighting infection. Despite therapy, recurrent disease is seen in 10-35% of patients after their initial case of CDI and in 35-65% of patients after primary reoccurrence,[1] stressing the need for more effective therapies. It has been hypothesized that the degree of disease severity correlates with the intensity of the host response. Therefore, a better understanding of the mechanism by which immune response provides production is important to develop therapies that modulate the host inflammatory response as a novel way to treat disease.

There is a long felt need in the art for compositions and methods useful for preventing and treating *C. difficile* infections. The present invention satisfies this need.

SUMMARY OF THE INVENTION

It is disclosed herein that IL-25 expression is decreased during antibiotic treatment and during bacterial infection and that treatment with IL-25 protein is protective during infection. It is further disclosed herein the unexpected result that IL-25 treatment protects against *C. difficile*-associated mortality and morbidity. The present application further describes an unexpected result regarding eosinophils and their role in combating infection and their relationship to the effectiveness of IL-25. In one aspect, IL-25 treatment induces protection by regulating the immune response. It is further disclosed that methods for stimulating IL-25 expression, levels, or activity during bacterial infections are also useful as treatments for the infection. The present invention encompasses compositions and methods useful to treat or prevent *Clostridium difficile* antibiotic-associated colitis through administration of IL-25 and/or downstream cytokines IL-13, IL-4, and IL-5.

The present invention provides compositions and methods useful for preventing or treating *Clostridium difficile* infection. In one aspect, the present invention provides for targeting multiple pathways. These include, for example, targeting IL-25 and its signaling pathways.

Various prior disease states and conditions are known to increase susceptibility to *C. difficile* infection. The present invention provides compositions and methods for prophylactically treating susceptible subjects to reduce the severity of an infection or to prevent infection by pre-treating the subject with a composition of the invention. One of ordinary skill in the art can determine if a subject is susceptible to CDI and can design a treatment regimen accordingly. In one embodiment, the invention provides compositions and methods useful for prevention of a *C. difficile* infection in a subject who becomes susceptible to a *C. difficile* infection. In one embodiment, a subject becomes susceptible to *C. difficile* infection due to prior antibiotic therapy that may lead to *C. difficile* infection. In one embodiment, a subject becomes susceptible to *C. difficile* infection due to prior H-2 blocker therapy. In one embodiment, a subject becomes susceptible to *C. difficile* infection due to a prior stem cell transplant. In one embodiment, a subject becomes susceptible to *C. difficile* infection due to a prior *C. difficile* infection and treatment for that prior infection. In one aspect, the compositions and methods of the invention prevent *C. difficile* infection. In one aspect, the compositions and methods of the invention reduce the severity of a new *C. difficile* infection when treatment is provided prophylactically (see FIG. 17). In one aspect, pretreatment with IL-25 or another compound or agent of the invention in an individual susceptible to CDI prevents CDI when the subject is exposed to *C. difficile*. In one aspect, pretreatment reduces severity of a CDI. In one aspect, pretreatment reduces morbidity. In one aspect, pretreatment prevents death in a susceptible subject who becomes infected.

In one aspect, the method comprises administering to a subject an effective amount of IL-25, or a biologically active fragment or homolog thereof, and/or downstream cytokines IL-13, IL-4, and IL-5.

In one aspect, pretreatment with IL-25 is protective during *C. difficile* infection. In one aspect, pretreatment with IL-25 increases survival rate in *C. difficile* infected subjects. In one aspect, the survival rate is increased by at least about 10%. In another aspect, the survival rate is increased by at least about 25%. In another aspect, the survival rate is increased by at least about 50%. In another aspect, the survival rate is increased by at least about 75%. In one aspect, IL-25 treatment stimulates an inflammatory response. In one aspect, IL-25 treatment stimulates tissue repair processes. In one aspect, IL-25 treatment stimulates an increase in eosinophil recruitment to the lamina propria during infection. In one aspect, IL-25 stimulates IL-4 production in eosinophils. In one aspect, eosinophils are not protective in the absence of IL-25. In one aspect, IL-25 induces Th2-like responses during CDI. In one aspect, IL-25 stimulates anti-inflammatory responses. In one aspect, IL-25 treatment increase IL-10. In one aspect, IL-25 increases mucin. In one aspect, the treatment increases eosinophil numbers in the subject even when the subject is also being treated with antibiotics.

In one aspect, IL-25 treatment decrease IL-23. In one aspect, IL-25 has no effect on neutrophils.

Doses of IL-25 can vary depending on the age, sex, weight, and health of the subject and a dosage regimen or strategy can be developed by one of ordinary skill in the art. In one aspect, a dose can be about 1.25 µg per 20 grams body weight and in another aspect, about 1.25 µg per 30 grams body weight.

The present application further discloses the role of IL-25 signaling in response to *C. difficile* infection and a means of using IL-25 and its signaling pathways for treatment.

The invention further provides compositions and methods for treating a *C. difficile* infection comprising administration of a pharmaceutical composition useful for stimulating recruitment of eosinophils in the gut, or an inducer of IL-4 production by eosinophils in the gut. In one aspect, infection can be treated by administration of eosinophils.

The present invention further encompasses the use of combination therapies comprising the administration of two or more of the following: IL-25 or stimulators of IL-25; stimulators of eosinophils; microbiota, use of precision microbiome reconstitution of the gut; use of bacteria that reduce susceptibility to *C. difficile* infection (such as *C. scindens*).

In one embodiment, useful bacteria include those that induce IL-25 when administered to a subject. In one embodiment, useful bacteria include those that are protective against *C. difficile*. Useful bacteria for the methods of the invention include, but are not limited to, *Helicobacter pylori*, a *Lactobacillus* species, an *Oxalobacter* species, *Clostridium scindens*, *C. populati*, *C. vincentii*, *C. irregulare*, *Blautia hansenii*, *Eubacterium contortum*, *Ruminococcus torques*, *Pseudoflavonifractor capillosus*, *Anaerostipes* sp., *Staphylococcus warneri*, *Lactobacillus reuteri*, *Enterococcus hirae*, *Enterorhabdus* sp. nov., and *Bacteroidetes* sp. nov.

The present invention further provides compositions and methods useful for diagnosing CDI, for monitoring the progression of CDI, and for monitoring the treatment of CDI. In one aspect, the diagnostic is based on changes in eosinophil levels. Additionally, treatment can be based on the results of the levels of eosinophils. One of skill in the art can determine when or how to treat a subject as well as when treatment can cease. The results of the tests can also be used to determine what type of treatment should be used. In one aspect, an increased in eosinophil levels during treatment is an indication that the treatment is working. In one aspect, the treatment comprises administering IL-25 or biologically active fragments and homologs thereof.

The present invention further provides compositions and methods for identifying agents useful for treating and preventing CDI. These methods include tests to assay changes in parameters disclosed herein to be involved in CDI infection and treatment such as the role of IL-25, changes in eosinophil levels, certain bacteria that can induce IL-25 or can be protective against CDI, and changes in bacteria, all of which have an impact on treatment. The Examples provide compositions and method for identifying such agents, including various types of compounds and bacteria.

The present invention further provides a kit comprising at least one active compound of the invention, optionally a pharmaceutically-acceptable carrier, optionally an additional therapeutic agent, an applicator, and an instructional material. In one aspect, the compound is IL-25 or a biologically active fragment or homolog thereof.

Various aspects and embodiments of the invention are described in further detail below.

BRIEF DESCRIPTION OF THE DRAWINGS

FIG. 11: How does IL-25 skew the immune response in the absence of CDI? Upper Panel graphically illustrates that IL-25 treatment in the presence of antibiotics increases the number of eosinophils relative to the number in antibiotic treated animals not receiving IL-25 treatment. Lower Panel graphically illustrates the effect of IL-25 on eosinophils IL-4+.

FIG. 18: IL-25 signaling protects against epithelial disruption but does not alter *C. difficile* burden. IL-25 reduces epithelial disruption (damage) in the colon on day 3 post infection (micrographs and upper graph). IL-25 treatment does not impact bacterial burden (see lower graphs), suggesting protection is mediated via influences on immune responses (n=12). Upper Photomicrograph—PBS treated; Lower Photomicrograph—rIL-25 treated; Upper Graph—Histology Scores; Lower Left Graph—Toxin A/B levels in PBS or rIL-25 treated; Lower Right Graph—CFU in PBS or rIL-25 treated.

DETAILED DESCRIPTION

Figure 1:
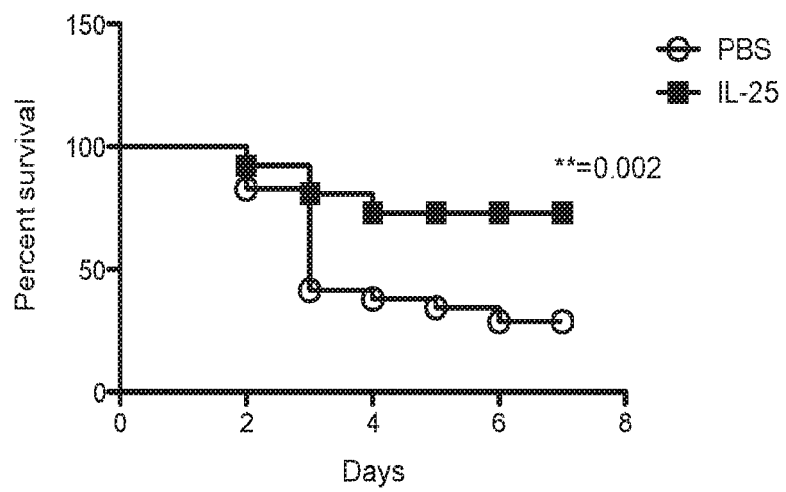
FIG. 1: Survival of IL-25 treated *C. difficile*-infected animals. Graphic illustration that IL-25 is protective during *C. difficile* infection as measured by percent survival.

Abbreviations and Acronyms
ABX—antibiotic
CDI—*Clostridium difficile* infection
CFU—colony forming unit
FMT—fecal microbiota transplantation
IL-25—Interleukin 25
kg—kilogram
mg—milligram
OTU—operational taxonomic unit
PBS—phosphate buffered saline
rIL-25—recombinant IL-25
Siglec-F—sialic acid-binding immunoglobulin-like lectin F
UT—untreated
VPI 10463—a strain of *C. difficile*
Definitions As used herein, the terms below are defined by the following meanings:

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

An "agent" useful for treating a *C. difficile* infection, as used herein means any compound, molecule, or cell that can directly or indirectly be used to treat an infection. Cells can include, for example, eosinophils or one of more types of bacteria. Such an "agent" can also be referred to as a "useful agent".

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both. A "therapeutic" treatment is a treatment administered to a subject who exhibits signs of pathology for the purpose of diminishing or eliminating those signs.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

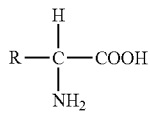

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin subunit molecules. The antibodies in the present invention may exist in a variety of forms including, for example, polyclonal antibodies, monoclonal antibodies, Fv, Fab and F(ab)2, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "secondary antibody" refers to an antibody that binds to the constant region of another antibody (the primary antibody).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "at least two antibiotics", as used herein, means at least two different antibiotics.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands. "Binding partner," as used herein, refers to a molecule capable of binding to another molecule.

The term "biological sample," as used herein, refers to samples obtained from a subject, including, but not limited to, skin, hair, tissue, blood, plasma, serum, cells, sweat, saliva, feces, tissue and/or urine.

As used herein, the term "biologically active fragments" or "bioactive fragment" of the polypeptides encompasses natural or synthetic portions of the full length protein that are capable of specific binding to their natural ligand or of performing the function of the protein. For example, a "functional" or "active" biological molecule is a biological molecule in a form in which it exhibits a property by which it is characterized. A functional enzyme, for example, is one which exhibits the characteristic catalytic activity by which the enzyme is characterized.

"Co-administer" can include simultaneous and/or sequential administration of two or more agents.

A "compound," as used herein, refers to any type of substance or agent that is can be considered a drug, or a candidate for use as a drug, as well as combinations and mixtures of the above.

The terms "comprises", "comprising", and the like can have the meaning ascribed to them in U.S. Patent Law and can mean "includes", "including" and the like. As used herein, "including" or "includes" or the like means including, without limitation.

As used herein, the term "conservative amino acid substitution" is defined herein as an amino acid exchange within one of the following five groups:
 I. Small aliphatic, nonpolar or slightly polar residues:
  Ala, Ser, Thr, Pro, Gly;
 II. Polar, negatively charged residues and their amides:
  Asp, Asn, Glu, Gln;
 III. Polar, positively charged residues:
  His, Arg, Lys;
 IV. Large, aliphatic, nonpolar residues:
  Met Leu, Ile, Val, Cys
 V. Large, aromatic residues:
  Phe, Tyr, Trp "Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" generally means an amount which provides the desired local or systemic effect, such as enhanced performance. For example, an effective dose is an amount sufficient to affect a beneficial or desired clinical result. The dose could be administered in one or more administrations and can include any preselected amount. The precise determination of what would be considered an effective dose may be based on factors individual to each subject, including size, age, injury or disease being treated and amount of time since the injury occurred or the disease began. One skilled in the art, particularly a physician, would be able to determine what would constitute an effective dose.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide. The terms "fragment" and "segment" are used interchangeably herein. As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length. As used herein, the term "fragment" as applied to a nucleic acid, may ordinarily be at least about 20 nucleotides in length, typically, at least about 50 nucleotides, more typically, from about 50 to about 100 nucleotides, at least about 100 to about 200 nucleotides, at least about 200 nucleotides to about 300 nucleotides, at least about 300 to about 350, at least about 350 nucleotides to about 500 nucleotides, at least about 500 to about 600, at least about 600 nucleotides to about 620 nucleotides, at least about 620 to about 650, and or the nucleic acid fragment will be greater than about 650 nucleotides in length.

As used herein, "health care provider" includes either an individual or an institution that provides preventive, curative, promotional or rehabilitative health care services to a subject, such as a patient.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul [50; 1990]), modified as in Karlin and Altschul [51; 1993]. This algorithm is incorporated into the NBLAST and XBLAST programs of Altschul, et al. [52], and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. [53]. Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide or antibody of the invention in the kit for diagnosing or effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The terms "intestinal microbiota", "gut flora", and "gastrointestinal microbiota" are used interchangeably to refer to bacteria in the digestive tract.

The term "isolated" refers to a compound, including antibodies, nucleic acids or proteins/peptides, or cell that has been separated from at least one component which naturally accompanies it.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "microbiota" refers to an assemblage of microorganisms localized to a distinct environment.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

"Pharmaceutically acceptable" means physiologically tolerable, for either human or veterinary application.

As used herein, "pharmaceutical compositions" include formulations for human and veterinary use.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, the term "probiotic" refers to a substantially pure bacteria (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, milk, yogurt, infant formula, and other dairy products.

As used herein, the term "prebiotic" refers to an agent that increases the number and/or activity of one or more desired bacteria. Non-limiting examples of prebiotics useful in the methods of the present invention include fructooligosaccharides (e.g., oligofructose, inulin, inulin-type fructans), galactooligosaccharides, amino acids, alcohols, and mixtures thereof.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

The term "reduces recurrent infection" means that the number or percentage of subjects who get another C. difficile infection following a low dose or short-term course of treatment for an initial C. difficile infection is lower compared to the number who had received standard doses or standard duration therapies.

The term "regulate" refers to either stimulating or inhibiting a function or activity of interest.

The term "standard," as used herein, refers to something used for comparison. For example, it can be a known standard agent or compound which is administered and used for comparing results when administering a test compound or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker. Standard can also refer to a healthy individual.

The term "stimulator of IL-25" as used herein means to stimulate or increase the expression, levels, or activity of IL-25 as described herein for treating C. difficile infection.

A "subject" is a vertebrate, including a mammal, such as a human. Mammals include, but are not limited to, humans, farm animals, sport animals, and pets.

The term "substantially pure" describes a compound, e.g., a protein or polypeptide, cell or nucleic acid that has been separated from components which naturally accompany it. Typically, a compound is substantially pure when at least 10%, including at least 20%, at least 50%, at least 60%, at least 75%, at least 90%, at least 95%, at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

As used herein, a "substantially homologous amino acid sequences" or "substantially identical amino acid sequences" includes those amino acid sequences which have at least about 92%, or at least about 95% homology or identity, including at least about 96% homology or identity, including at least about 97% homology or identity, including at least about 98% homology or identity, and at least about 99% or more homology or identity to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" or "substantially identical nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. In one embodiment, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 92%, 95%, 99% or more. Substantial identity of nucleic acid sequences can be determined by comparing the sequence identity of two sequences, for example by physical/chemical methods (i.e., hybridization) or by sequence alignment via computer algorithm.

Suitable nucleic acid hybridization conditions to determine if a nucleotide sequence is substantially similar to a reference nucleotide sequence are: 7% sodium dodecyl sulfate SDS, 0.5 M NaPO4, 1 mM EDTA at 50° C. with washing in 2× standard saline citrate (SSC), 0.1% SDS at 50° C.; preferably in 7% (SDS), 0.5 M NaPO4, 1 mM EDTA at 50° C. with washing in 1×SSC, 0.1% SDS at 50° C.; preferably 7% SDS, 0.5 M NaPO4, 1 mM EDTA at 50° C. with washing in 0.5×SSC, 0.1% SDS at 50° C.; and more preferably in 7% SDS, 0.5 M NaPO4, 1 mM EDTA at 50° C. with washing in 0.1×SSC, 0.1% SDS at 65° C. Suitable computer algorithms to determine substantial similarity between two nucleic acid sequences include, GCS program package. The default settings provided with these programs are suitable for determining substantial similarity of nucleic acid sequences for purposes of the present invention.

By the term "susceptible to *C. difficile* infection", as used herein, refers to a subject who, due to a prior disease state, treatment, or condition has now become more susceptible to such an infection than if they had not had the prior disease, treatment, or condition. Such susceptible subjects are described herein and others are also known in the art.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "treat," "treating", or "treatment" includes treating, ameliorating, or inhibiting an injury or disease related condition or a symptom of an injury or disease related condition. In one embodiment the disease, injury or disease related condition or a symptom of an injury or disease related condition is prevented; while another embodiment provides prophylactic treatment of the injury or disease related condition or a symptom of an injury or disease related condition. The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

Embodiments

The present application provides compositions and methods useful for preventing or treating a *Clostridium difficile* (*C. difficile*) infection in a subject in need thereof. In one embodiment, the method comprises administering to the subject a pharmaceutical composition comprising a pharmaceutically-acceptable carrier, an effective amount of IL-25 or biologically active fragments or homologs thereof or an effective amount of a stimulator of IL-25. In one aspect, the composition further comprises an additional therapeutic agent. In one aspect, IL-25 is recombinant IL-25. In one aspect, the method increases survival of the subject. In one aspect, the method stimulates eosinophil recruitment to the lamina propria layer of the intestine. In one aspect, the method induces IL-4 synthesis in eosinophils. In one aspect, the method stimulates eosinophil recruitment or levels in the colon. In one aspect, the colon is the sigmoid colon. In one aspect, the method stimulates mucin expression. In one aspect, the mucin expression increases in lamina propria of the intestine. In one aspect, the method stimulates IL-10 expression in eosinophils. In one aspect, successful treatment requires the presence of eosinophils. In one aspect, the subject is treated before the infection as a preventative measure. In one aspect, the treatment reduces morbidity and mortality. In one aspect, the method inhibits epithelial disruption by *C. difficile* in the colon. In one aspect, the method does not alter the *C. difficile* burden nor does it stimulate neutrophil recruitment. In one aspect, the method decreases IL-23 expression or levels.

In one aspect, the treatment increases survival of the subject by about 10% to about 68% compared to a subject not receiving the treatment. In one aspect, the method increases survival of the subject by about 45% compared to a subject not receiving the treatment.

In one embodiment, IL-25 or biologically active fragments or homologs thereof are administered at a dose of about 1.0 µg IL-25/kilogram (kg) body weight to about 2500 µg IL-25/kg body weight. In one aspect, IL-25 or biologically active fragments or homologs thereof are administered at a dose of about 10 µg IL-25/kg body weight to about 1500 µg IL-25/kg body weight. In one aspect IL-25 or biologically active fragments or homologs thereof are administered at a dose of about 25 µg IL-25/kg body weight to about 500 µg IL-25/kg body weight. In one aspect, IL-25 or biologically active fragments or homologs thereof are administered at a dose of about 25 µg IL-25/kg body or about 62.5 µg IL-25/kg body weight.

In one embodiment, a stimulator of IL-25 is selected from the group consisting of metronidazole, a probiotic composition comprising one or more bacterial strains, a fecal sample, one or more bacterial species, microbiota derived from a fecal sample, and a prebiotic. Metronidazole is a useful antibiotic in practicing some of the methods of the invention based on effects it has as disclosed herein.

In one embodiment, the method prevents recurrent *C. difficile* infection in a subject susceptible to recurrent infection.

In one embodiment, the present invention provides compositions and methods useful for preventing *C. difficile* infection in a subject susceptible to such an infection because the subject has had prior antibiotic therapy.

In one embodiment, the method prevents *C. difficile* infection in a subject susceptible to CDI because the subject had prior H-2 blocker therapy or stem cell transplant, which renders a subject susceptible to CDI.

In one embodiment, the present invention provides compositions and methods for treating a *C. difficile* infection in a subject by stimulating IL-25 expression or signaling. In one aspect, the method comprises administering to a subject a composition comprising an effective amount of an agent selected from the group consisting of a probiotic composition comprising one or more bacterial strains, a fecal matter sample, microbiota derived from a fecal matter sample, and a prebiotic, wherein the treatment stimulates IL-25 expression or signaling.

In one aspect, the microbiota comprises gastrointestinal microbiota.

In one aspect, the probiotic of the invention comprises at least one of *Helicobacter pylori*, a *Lactobillus* species, an *Oxalobacter* species, *Clostridium scindens, C. populati, C. vincentii, C. irregulare, Blautia hansenii, Eubacterium contortum, Ruminococcus torques, Pseudoflavonifractor capillosus, Anaerostipes* sp., *Staphylococcus warneri, Lactobacillus reuteri, Enterococcus hirae, Enterorhabdus* sp. nov., and *Bacteroidetes* sp. nov.

In one aspect, the probiotic composition comprises one or more bacteria isolated from microbiota.

In one aspect, when the agent to be administered is bacteria, the bacteria are administered in an effective amount wherein the amount is sufficient to achieve colonization of the gastrointestinal tract.

In one aspect, the bacteria are administered as an inoculant selected from the group consisting of about $1\times10^3$, $10^4$, $10^5$, $10^6$, $10^7$, $10^8$, $10^9$, and $10^{10}$ CFU.

In one aspect, the bacteria are selected from the group consisting of *Helicobacter pylori*, a *Lactobillus* species, an *Oxalobacter* species, *Clostridium scindens, C. populati, C. vincentii, C. irregulare, Blautia hansenii, Eubacterium contortum, Ruminococcus torques, Pseudoflavonifractor capillosus, Anaerostipes* sp., *Staphylococcus warneri, Lactobacillus reuteri, Enterococcus hirae, Enterorhabdus* sp. nov., and *Bacteroidetes* sp. nov.

In one embodiment, the treatment comprises administering a conditional lethal bacterial strain.

In one embodiment, when prebiotic is used it is selected from the group consisting of fructooligosaccharides, galactooligosaccharides, amino acids, alcohols, and mixtures thereof. In one aspect, the fructooligosaccharide is selected from the group consisting of oligofructose, inulin, and inulin-type fructans.

In one embodiment, the present invention provides compositions and methods useful for treating a *C. difficile* infection comprising administering to a subject a pharmaceutical composition comprising a pharmaceutically-acceptable carrier, an effective amount of a stimulator of eosinophil recruitment in the gut or an effective amount of an inducer of IL-4 production by eosinophils in the intestine, and optionally an additionally therapeutic agent, thereby treating said *C. difficile* infection. In one aspect, the stimulator is IL-25 or a biologically active fragment or homolog thereof. In one aspect, the inducer of IL-4 production by eosinophils in the gut is IL-25 or biologically active fragments or homologs thereof. In one aspect, the stimulator is selected from the group consisting of probiotic composition comprising one or more bacterial strains, a fecal sample, microbiota derived from a fecal sample, and a prebiotic. In one aspect, the inducer of IL-4 production by eosinophils in the intestine is selected from the group consisting of a probiotic composition comprising one or more bacterial strains, a fecal sample, microbiota derived from a fecal sample, and a prebiotic. In one aspect, when the pharmaceutical composition comprises bacteria, said bacteria are selected from the group consisting of *Helicobacter pylori*, a *Lactobillus* species, an *Oxalobacter* species, *Clostridium scindens, C. populati, C. vincentii, C. irregulare, Blautia hansenii, Eubacterium contortum, Ruminococcus torques, Pseudoflavonifractor capillosus, Anaerostipes* sp., *Staphylococcus warneri, Lactobacillus reuteri, Enterococcus hirae, Enterorhabdus* sp. nov., and *Bacteroidetes* sp. nov.

The present invention further provides a method for preventing or treating a *C. difficile* infection in a subject in need thereof, comprising determining the level of eosinophils present in the intestine or fecal matter of the subject, wherein when a lower level of eosinophils is measured in the subject compared to the level of eosinophils in a control or standard sample of eosinophils is an indication of *C. difficile* infection and the subject is treated for said *C. difficile* infection. In one aspect, the subject is treated by administering a composition selected from the from the group consisting of an effective amount of an inducer of eosinophils, eosinophils, IL-25, a probiotic composition comprising one or more bacterial strains, a fecal sample, microbiota derived from a fecal sample, and a prebiotic.

The present invention further provides compositions and methods useful for diagnosing a *C. difficile* infection in a subject. The method can also be coupled with treatment of the subject. In one aspect, the diagnostic method comprises measuring the level of eosinophils in the subject, wherein a lower level of eosinophils in the subject compared to the level of eosinophils in a control sample or a sample obtained from an otherwise identical second subject infected with *C. difficile* is an indication that said subject is infected with said *C. difficile*.

In one aspect, the eosinophils are intestinal eosinophils or fecal matter eosinophils. In one aspect, the eosinophils are measured in a biological sample obtained from the subject. In one aspect, the sample is selected from the group consisting of a biopsy, fecal matter, and blood. In one aspect, the biopsy is an intestinal biopsy. In one aspect, the intestinal biopsy is a biopsy of the colon. In one aspect, the colon is sigmoid colon.

The present invention further provides a method for monitoring the treatment of a subject infected with *C. difficile* or for monitoring the progression of an infection. In one embodiment, the method comprises determining the level of eosinophils in the subject being treated for a *C. difficile* infection and comparing the levels to the pretreatment level of eosinophils in the subject, wherein an increase in the level of eosinophils in the subject being treated is an indication that the treatment is effective, further wherein a decrease in the level of eosinophils or no increase in the level of eosinophils during treatment is an indication that said treatment is ineffective. When progression is being monitored, the measured levels can be used to help determine when and if treatment should begin and what kind of treatment should be used.

In one aspect, the treatment is modified if the eosinophil levels measured in the subject being treated have not returned to a normal level or have not increased relative to the pre-treatment level of eosinophils in the subject. One of ordinary skill in the art can determine how to modify the treatment.

The present invention further provides a method for identifying an agent or combination of agents useful treating for a *C. difficile* infection. The method comprises administering to a test subject a composition comprising an agent or combination of agents and determining whether the agent or combination of agents stimulates a desirable effect in the test subject. The effect is selected from the group consisting of increasing recruitment of eosinophils in the intestine, increasing eosinophil levels in the intestine, increasing eosinophils in the fecal matter, increasing eosinophil levels in the blood, increasing IL-4 production by eosinophils in the intestine, increasing IL-25 levels or activity in the intestine, increasing IL-10 expression in the intestine, and increasing mucin 2 levels in the intestine. In one aspect, the test subject is infected with *C. difficile*. In one aspect, the test subject is murine or human. In one aspect, the composition is selected from the group consisting of a probiotic composition comprising one or more bacterial strains, a fecal sample, microbiota derived from a fecal sample, and a prebiotic.

The present invention further encompasses agents or combinations of agents identified using the methods of the invention.

In one aspect, the method of identifying useful agents is useful for identifying specific bacteria, probiotic compositions, microbiota, or microbiota components with *C. difficile* infection-treating activity. In one aspect the bacteria are selected from the group consisting of *Helicobacter pylori*, a *Lactobillus* species, an *Oxalobacter* species, *Clostridium scindens*, *C. populati*, *C. vincentii*, *C. irregulare*, *Blautia hansenii*, *Eubacterium contortum*, *Ruminococcus torques*, *Pseudoflavonifractor capillosus*, *Anaerostipes* sp., *Staphylococcus warneri*, *Lactobacillus reuteri*, *Enterococcus hirae*, *Enterorhabdus* sp. nov., and *Bacteroidetes* sp. nov.

The invention further provides a method for preventing or treating a *C. difficile* infection. The method comprises administering to a subject in need thereof a pharmaceutical composition comprising an effective amount of one or more agents identified by the method described herein.

*Clostridium difficile* infection (CDI) is a significant cause of antibiotic-associated nosocomial diarrhea. While discontinuation of the offending antibiotic is the ideal strategy to control the disease, in most cases, treatment with antimicrobial agents active against *C. difficile* is deemed necessary because of the severity of the gastrointestinal disease or the presence other active infections. Unfortunately, antimicrobial treatment for a first episode of CDI is associated with up to 25% recurrence of the disease. Alteration of the indigenous intestinal flora is critical to susceptibility to CDI and its recurrence. Antibiotic treatment may further disrupt the already abnormal flora and thereby enhance the growth of any leftover *C. difficile* organisms or of a newly acquired strain once antibiotics are discontinued.

After one incidence of recurrence, rates increase to up to 60%. A recurrence rate of up to almost 50% has been noted with metronidazole use. Even in the carrier state, it had been shown that treatment with either metronidazole or vancomycin of individuals with *C. difficile* is associated with the reisolation of the organism in the stool 2 months later, with recurrence not necessarily coming from the original strain. The recent epidemic saw the increasing failure of metronidazole to cure CDI. Vancomycin is now the drug of choice for severe disease.

It has been hypothesized that the intensity of the host response and resulting inflammation may be correlated with disease severity. Understanding and targeting host-based mediators of inflammation may provide a target for more effective therapy.

The present invention encompasses the use of IL-25 as a treatment for CDI. Useful IL-25 proteins, homologs, and fragments thereof include those with the activity described herein. These include, for example, those with GenBank Accession Numbers AAH69565.1 (SEQ ID NO:1), AAI04932.1 (SEQ ID NO:2), AAI04930.1 (SEQ ID NO:2), NP_758525.1 (SEQ ID NO:2), NP_073626.1 (SEQ ID NO:1), and biologically active fragments and homologs thereof. Non-human IL-25 peptides with the activity described herein are also encompassed by the present invention. The invention further encompasses the use of recombinant IL-25 (rIL-25).

One of ordinary skill in the art will appreciated that the dose of IL-25 (or biologically active fragments and homologs thereof) can be varied depending on such things as the age, health, sex, and age of the subject as well as the severity of the CDI or whether it is being used as a preventative. For example, mice received 0.5 ug to 1.25 ug of recombinant IL-25 intraperitoneally daily for 5 days prior to infection or for various amounts of time. The mice are approximately 20 grams in weight. When this dose is translated to humans, the dose would be approximately 25 ug of rIL-25/kg body weight to about 62.5 ug of rIL-25/kg body weight. Additionally, depending on various parameters regarding the subject, whether a dose is provided in one administration to a subject or as multiples, the present invention further encompasses doses of about 1.0 ug/kg body weight to about 250 ug/kg body weight. In one aspect, the range is about 2.0 to about 150 ug IL-25/kg body weight. In another aspect, the range is about 5.0 to about 100 ug/kg body weight. In yet another aspect, the dose range is about 10 to about 75 ug/kilo body weight. In a further aspect, the range is about 20 to about 50 ug/kg body weight. The doses include fractions and decimals of the doses provided herein. In one aspect, the therapeutically effective dose used is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 58, 59, 60, 61, 62, 62.5, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 ug IL-25/kg body weight., and decimals thereof.

In one embodiment, a dose of about 2.5-250 ug/kg of recombinant IL-25 administered daily for 5 days may be effective at reducing CDI-associated mortality rates in humans. In one aspect, it is administered for 1, 2, 3, 4, 5, 6, 7, 8, 9, or 10 days.

Alternatively, a single dose of about 12.5-1250 ug/kg of recombinant administered only once may be effective at reducing CDI-associated mortality rates in humans.

One of ordinary skill in the can determine the method and site of administration. For example, intravenous or subcutaneous injection of IL-25 protein would be an effective treatment.

A compound of the invention can be administered once or more than once. It can be administered once a day or at least twice a day. In one aspect, a compound is administered every other day within a chosen term of treatment. In one embodiment, at least two compounds of the invention are used. One of ordinary skill in the art can determine how often to administer a compound of the invention, the duration of treatment, and the dosage to be used.

Treatment of CDI as described herein is useful for prevention of relapse or reinfection, as well as reducing the frequency of relapse or reinfection.

In one embodiment, the present invention provides compositions and therapeutic methods involving the use of probiotics, prebiotics, or narrow spectrum antibiotics/antibacterial agents that are capable of restoring healthy mammalian bacterial gastrointestinal microbiota.

In one embodiment, targeted restoration of the intestinal microbiota is used to prevent or treat relapsing *C. difficile* infection or increase resistance to infection (see Lawley et al., PLOS Pathogens, 2012 and Buffie et al., Nature, 2015). In one aspect, these treatments can be used in conjunction with other therapies disclosed herein. The present invention provides for targeting a dysbiotic microbiota with a defined mixture of diverse bacteria to change the microbial community in the intestine such that it displaces *C. difficile* or is resistant to *C. difficile*. In one embodiment, useful bacteria include those that induce IL-25 when administered to a subject. In one embodiment, useful bacteria include those that are protective against *C. difficile*. Useful bacteria for the methods of the invention include, but are not limited to, *Clostridium scindens, C. populati, C. vincentii, C. irregulare, Blautia hansenii, Eubacterium contortum, Ruminococcus torques, Pseudoflavonifractor capillosus, Anaerostipes* sp., *Staphylococcus warneri, Lactobacillus reuteri, Enterococcus hirae, Enterorhabdus* sp. nov., and *Bacteroidetes* sp. nov. For example, *Clostridium scindens, C. populati, C. vincentii, C. irregulare, Blautia hansenii, Eubacterium contortum, Ruminococcus torques*, and *Pseudoflavonifractor capillosus* were shown to be protective by Buffie et al., (2015, Nature). Also, *Anaerostipes* sp., *Staphylococcus warneri, Lactobacillus reuteri, Enterococcus hirae, Enterorhabdus* sp. nov., and *Bacteroidetes* sp. nov. were shown to be useful for restoration of the microbiota by Lawley et al. (PLOS Pathogens, 2012).

In one embodiment, the present invention provides compositions and methods for treating *C. difficile* infections by regulating the microbiota of the gut. In one aspect, the invention provides a method of treatment comprising administering to the subject a therapeutically effective amount of a probiotic composition comprising one or more bacterial strains, wherein the composition stimulates the growth or activity of one or more bacterial taxa which are under-represented in microbiota of the mammal as compared to a healthy control or inhibits the growth or activity of one or more bacterial taxa which are over-represented in microbiota of the mammal as compared to a healthy control. In one aspect, the treatment induces IL-25 signaling, expression, levels, or activity.

The present invention provides for treating CDI to reduce infection and to increase survival of subjects being treated. We have observed a 77% survival rate in CDI-infected mice treated with recombinant IL-25 compared to a 32% rate observed in PBS treated mice. From this data, we can estimate that human patients treated with recombinant IL-25 will have a 45% greater chance of surviving *C. difficile* infection than those not receiving IL-25. In one aspect, the compositions and methods of the invention are useful for increasing survival of a subject with CDI up to about 68%, 65, 60, 55, 50, 45, 40, 35, 30, 25, 20, 15, and 10% more than those not treated with IL-25. In one aspect, the range of survival improvement is about 10-68% more, or about 15-65% more, or about 20-60% more, or about 25-55% more, or about 30-50% more, or about 35-45% more than those not receiving IL-25. In absolute percentages, in one aspect, the compositions and methods of the invention when used to treat CDI yield a survival rate of about 99, 95, 90, 85, 80, 77, 75, 70, 65, 60, 55, 50, 45, 40, and 35%.

In one embodiment of the invention, a fecal sample or microbiota derived from a fecal sample is used to treat a subject in need thereof. In one aspect, the fecal sample is from a subject not infected with *C. difficile*. In one aspect, one or more bacteria species derived from a fecal sample are used.

Various bacteria can be used, for example, *H. pylori, Lactobillus* species, and *Oxalobacter* species.

Bacterial strains administered according to the methods of the present invention can comprise live bacteria. One or several different bacterial inoculants can be administered simultaneously or sequentially (including administering at different times). Such bacteria can be isolated from microbiota and grown in culture using known techniques. However, many bacterial species are very difficult to culture and administration of others (like *H. pylori*) may lead to various undesirable side-effects. The present invention therefore comprises administering "bacterial analogues", such as recombinant carrier strains expressing one or more heterologous genes derived from the bacteria affected in a disease. The use of such recombinant bacteria may allow the use of lower therapeutic amounts due to higher protein expression and may simultaneously avoid any potential harmful side-effects associated with reintroduction of specific bacterial strains. Non-limiting examples of recombinant carrier strains useful in the methods of the present invention include *E. coli* and *Lactobacillus* (e.g., *E. coli* and *Lactobacillus* expressing cag island-encoded type IV secretion system of *H. pylori*). Methods describing the use of bacteria for heterologous protein delivery are described, e.g., in U.S. Pat. No. 6,803,231.

Human fecal material is screened for the presence of pathogenic microorganisms prior to its use.

Fecal samples have been used, for example, to treat *C. difficile* colitis (Hlavka, U.S. Pat. Pub. No. U.S. 2014/0086877, published Mar. 27, 2014).

Administration of a bacterial inoculant can be accomplished by any method likely to introduce the organisms into the desired location. The bacteria can be mixed with a carrier and (for easier delivery to the digestive tract) applied to liquid or solid food or to drinking water. The carrier material should be non-toxic to the bacteria and the subject/patient. Preferably, the carrier contains an ingredient that promotes viability of the bacteria during storage. The formulation can include added ingredients to improve palatability, improve shelf-life, impart nutritional benefits, and the like. If a reproducible and measured dose is desired, the bacteria can be administered by a rumen cannula.

The dosage of the bacterial inoculant or compound of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the gastrointestinal tract with the desired bacterial inoculant, e.g. about $10^6$, $10^7$, $10^8$, $10^9$, and $10^{10}$ CFU for example. The dose can be administered as a single dose. In one embodiment, lower doses can be effective, including, but not limited to, about $10^3$, $10^4$, and $10^5$ CFU.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria die. Methods relating to conditional lethal strains of *H. pylori* are described in U.S. Pat. No. 6,570,004.

A compound of the invention can be administered once or more than once. It can be administered once a day or at least twice a day. In one aspect, a compound is administered every other day within a chosen term of treatment. In one embodiment, at least two compounds of the invention are used.

One of ordinary skill in the art can determine how often to administer a compound of the invention, the duration of treatment, and the dosage to be used. Factors used in such a determination include the severity of the infection, the age and health of the subject, the particular anti-*C. difficile* antibiotic being administered, and the route of administration.

Treatment of CDI as described herein is useful for prevention of relapse or reinfection, as well as reducing the frequency of relapse or reinfection.

One of ordinary skill in the art can determine the dose and term of treatment to be used.

When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. For example, the two compounds could be administered up to 10 minutes apart, up to 30 minutes apart, up to 1 hour apart, etc. In one aspect, one or more of the compounds can be administered more than once. In one aspect, a compound is administered at least twice. In another aspect, a compound is administered at least five times. In one aspect, the method is useful for low dose treatment. In one aspect, the method is useful for short-term treatment.

An effective dose as described herein is, in one aspect, one that is sufficient to treat infection and control diarrhea and weight loss in a subject infected with *C. difficile*. Moreover, with this strategy, the intestinal gut flora is preserved and recurrent disease is prevented.

In one aspect, an effective dose reduces mortality.

In one aspect, the compositions and methods of the invention are useful for preventing relapse in an already treated subject and in preventing reinfection.

One of ordinary skill in the art can determine the best route of administration of a pharmaceutical composition of the invention. For example, administration can be direct, enteral, or parenteral. Enteral includes, for example, oral and rectal administration. Parenteral includes, for example, intravenous administration.

The present invention further encompasses the use of therapeutically active homologs, analogs, and derivatives of the useful compounds of the invention.

The present invention further provides for the use of a unit dose.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" unless stated otherwise.

In one embodiment, at least one compound of the invention can be administered in conjunction with another therapeutic agent. Additional therapeutic agents include, for example, antibiotics, anti-diarrheals, steroids, anti-inflammatories, other antimicrobials, and inducers of chemokines. In one aspect, more than one therapeutic agent can be administered in conjunction with a therapeutic compound of the invention. Other antimicrobials include those drugs useful against infection other than a *C. diff.* infection where a subject may have need for treatment against an additional infection as well.

The present invention further provides kits comprising compounds of the invention, an applicator, and an instructional material for the use thereof.

Diarrhea

Inflammatory diarrhea occurs when there is damage to the intestinal mucosal lining or brush border, which leads to a passive loss of protein-rich fluids, and a decreased ability to absorb these lost fluids. Features of all three of the other types of diarrhea can be found in this type of diarrhea. It can be caused by bacterial infections, viral infections, parasitic infections, or autoimmune problems such as inflammatory bowel diseases. It can also be caused by tuberculosis, colon cancer, and enteritis.

Inflammatory diarrheas include those caused by enteric pathogens including, but not limited to, *Campylobacter jejuni, Salmonella* species, *Shigella* species, *Escherichia coli* (including enterohemorrhagic, enterotoxigenic, enteroaggregative *E. coli*), *Entamoeba histolytica, Clostridium difficile, Cryptosporidium* and those that have no clearly defined infectious agent such as, Crohn's Disease (CD) and ulcerative colitis (UC).

*Clostridium difficile* antibiotic-associated colitis is an increasing problem in health-care associated diarrhea, made more so recently by the emergence of a quinolone-resistant hyper-virulent strain. The infection is potentially fatal, difficult to treat, and prone to relapse.

Infectious diarrhea or contagious diarrhea may be defined as diarrhea caused by an infection of the digestive system by a bacterium, virus, or parasite that result in frequent bowel motions producing liquid feces. Viral diarrheas include, but are not limited to, those caused by Norovirus, Rotavirus, Adenovirus, or Astrovirus. Bacterial diarrheas, including diarrheas caused by their toxins, include, but are not limited to, diarrhea caused by *Campylobacter jejuni, Salmonella, Shigella, Vibrio cholerae/Cholera, Vibrio parahaemolyticus, Escherichia coli* (including enterohemorrhagic, enterotoxigenic, enteroaggregative *E. coli*), *Clostridium difficile*, staphylococcal toxin and *Bacillus cereus*.

Antimicrobials are substances that kill or inhibit the growth of microorganisms such as bacteria, fungi, virus, or protozoans. Antimicrobial drugs either kill microbes (microbiocidal) or prevent the growth of microbes (microbiostatic).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. For example, the active compound can be formulated to release only in the intestine and/or the colon.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary with the route of administration, the nature of the condition being treated and the age and condition of the patient and will be ultimately at the discretion of the attendant physician or clinician.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

EXAMPLE 1

It has been hypothesized that the degree of disease severity correlates with the intensity of the host response. Toxins secreted during *C. difficile* infection initiate the disruption of the intestinal epithelium. Epithelial cell death in turn is postulated to induce a pro-inflammatory cascade that leads to the recruitment of immune cells to the gut, which is hypothesized to cause further tissue destruction and disease severity. A hallmark of *C. difficile* infection is the trafficking of neutrophils to the site of barrier disruption. In fact, leukocytosis correlates to increased disease severity and a poor prognosis.[7] Additionally, recent studies indicate that inflammatory markers, such as IL-8, are a more accurate predictor of poor patient outcome than increased bacterial burden, emphasizing the importance of the immune response to control disease severity.[8]

Figure 2:
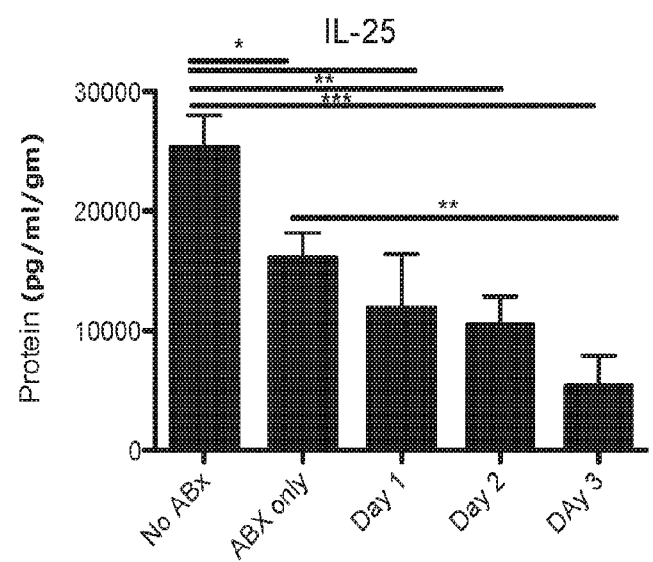
FIG. 2: Effect of antibiotic treatment on IL-25 expression in *C. difficile*-infected animals. IL-25 expression is decreased with antibiotic treatment and throughout the course of infection when compared with untreated controls. It is shown that IL-25 protein expression decreases during the infection. Groups listed as Days 1, 2, or 3 were infected.

We have found that pretreatment of mice with recombinant IL-25 protein is protective during *Clostridium difficile* infection (CDI) (FIG. 1). IL-25 is a Th2-like cytokine that signals upstream of IL-4, IL-5, and IL-13. Our data implicate that treatment or pretreatment with IL-25 and/or IL-4, IL-5, and IL-13 recombinant protein may be protective during human CDI. Th2-immunity is important in maintaining homeostasis in the gut. *C. difficile* pathology is mostly dependent on antibiotic pretreatment. Antibiotics cause a dysbiosis of the commensal bacteria providing a niche for colonization of *C. difficile*. Alterations in the microbiome are the foundation for susceptibility to many inflammatory diseases. It has been shown that IL-25 production is dependent on the commensal organisms of the microbiome.[9] We have been able to reproduce this data and establish that IL-25 protein expression in the gut is decreased during antibiotic treatment and remains reduced throughout the course of infection (FIG. 2).

Figure 3:
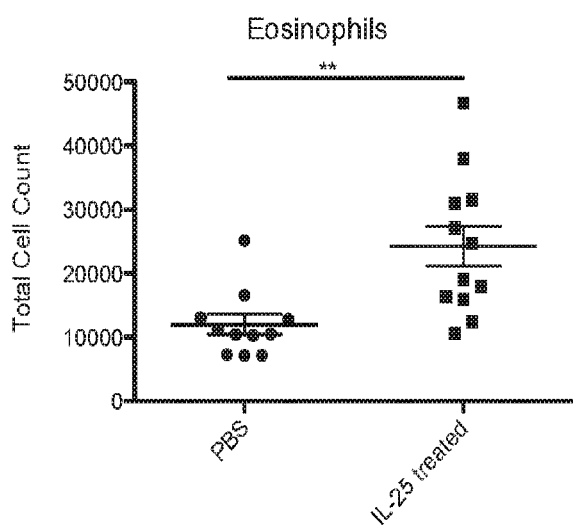
FIG. 3: Treatment of *C. difficile*-infected animals with IL-25. IL-25 administration is associated with increased eosinophil recruitment to the lamina propria on Day 3 of infection.
Figure 4:
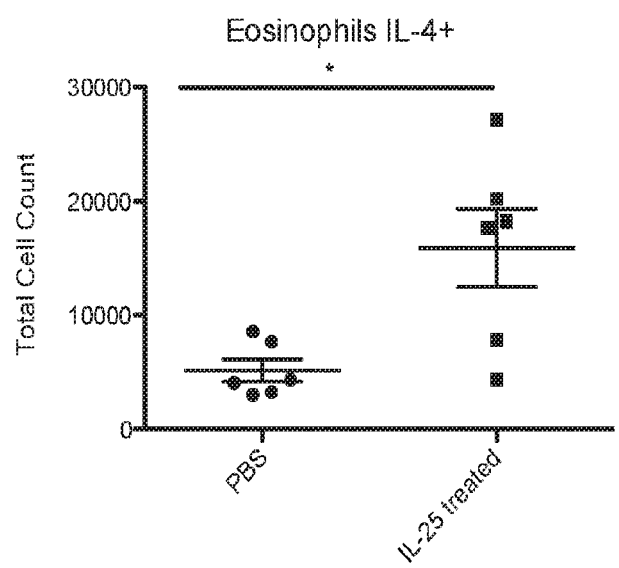
FIG. 4: Treatment of *C. difficile*-infected animals with IL-25. IL-25 induces IL-4 production from eosinophils in the lamina propria on Day 3 of infection.
Figure 5:
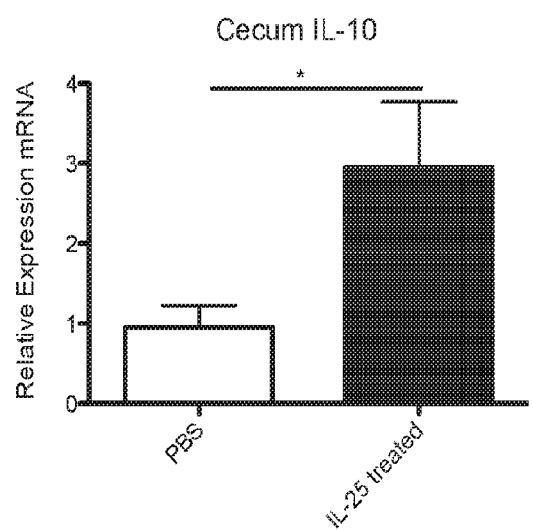
FIG. 5: Effect of *C. difficile* infection and IL-25 treatment on IL-10 expression. Anti-inflammatory (IL-10) responses are increased in cecal tissue with IL-25 treatment during infection, as determined by comparing relative mRNA expression of IL-25.
Figure 6:
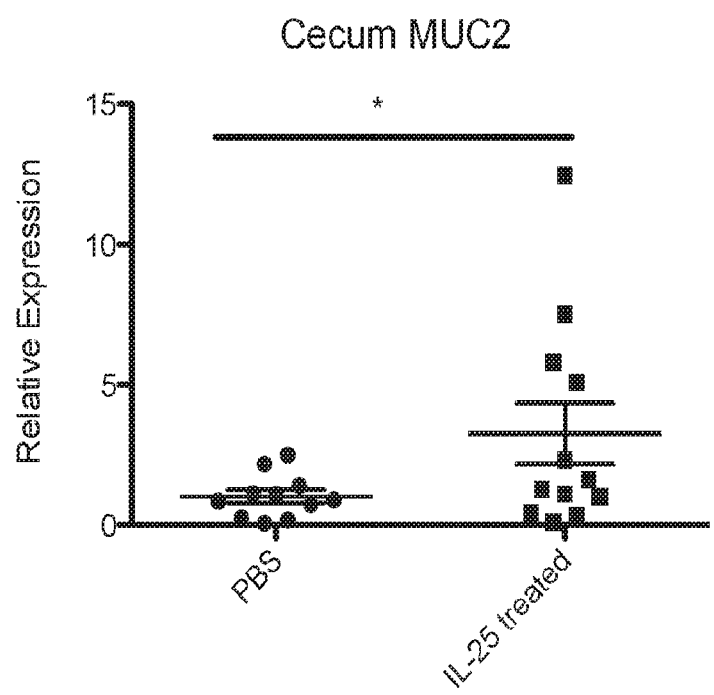
FIG. 6: Effect of IL-25 treatment on Mucin expression in *C. difficile*-infected animals. Mucin (MUC2) is enhanced in cecal tissue with IL-25 treatment during infection relative to treatment with PBS (control).
Figure 7:
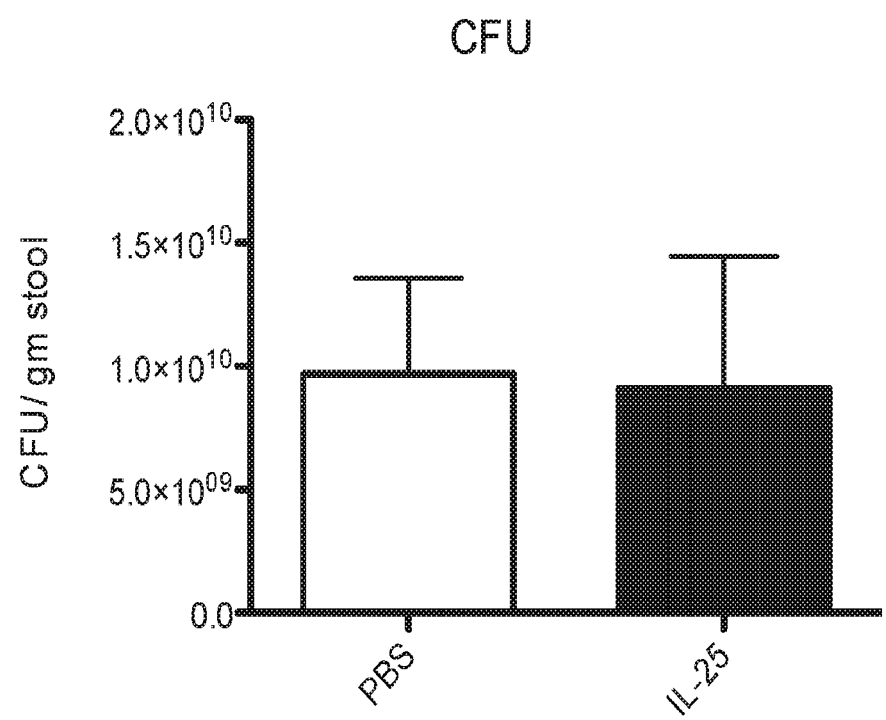
FIG. 7: IL-25 does not affect bacterial burden. As determined by measuring *C. difficile* CFU/gm stool.
Figure 8:
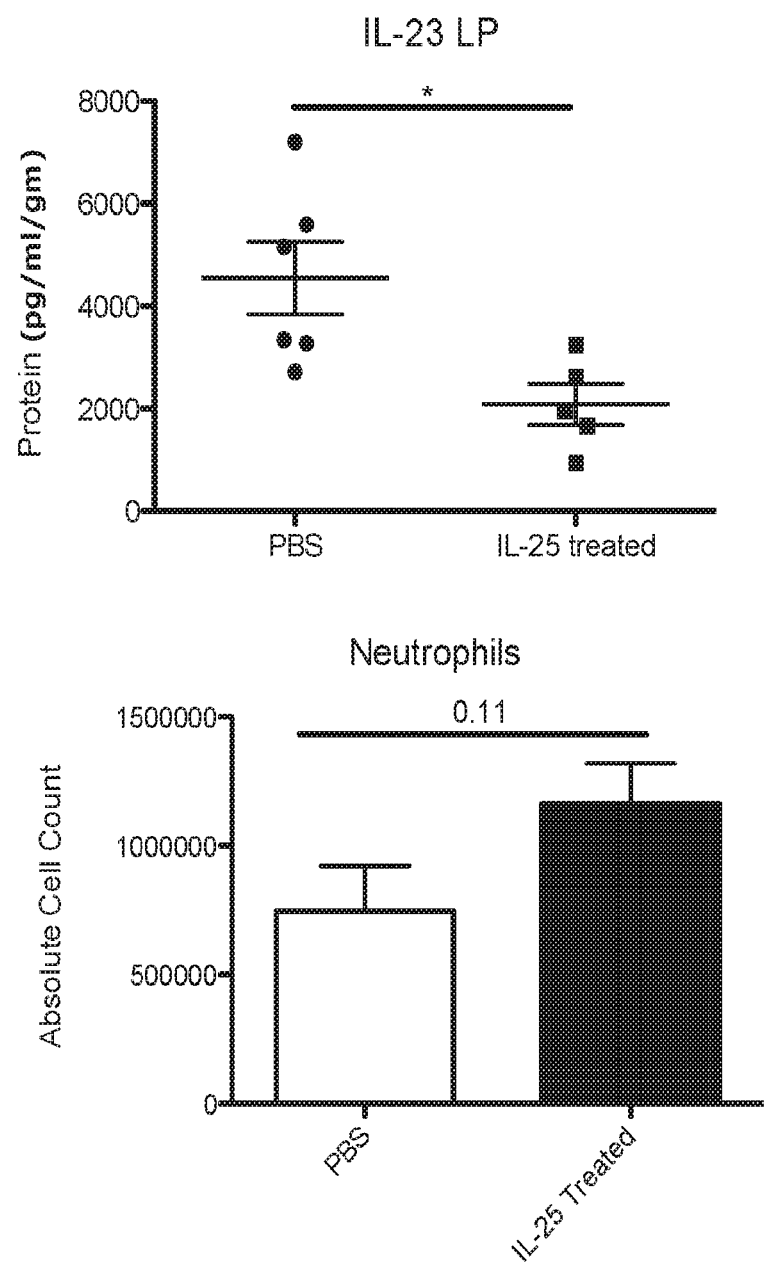
FIG. 8: IL-25 decreases IL-23, but has no effect on Neutrophils. Upper Panel graphically depicts IL-23 protein expression in control and IL-25 treated mice. Lower Panel graphically depicts the number of neutrophils in control and IL-25 treated mice.
Figure 9:
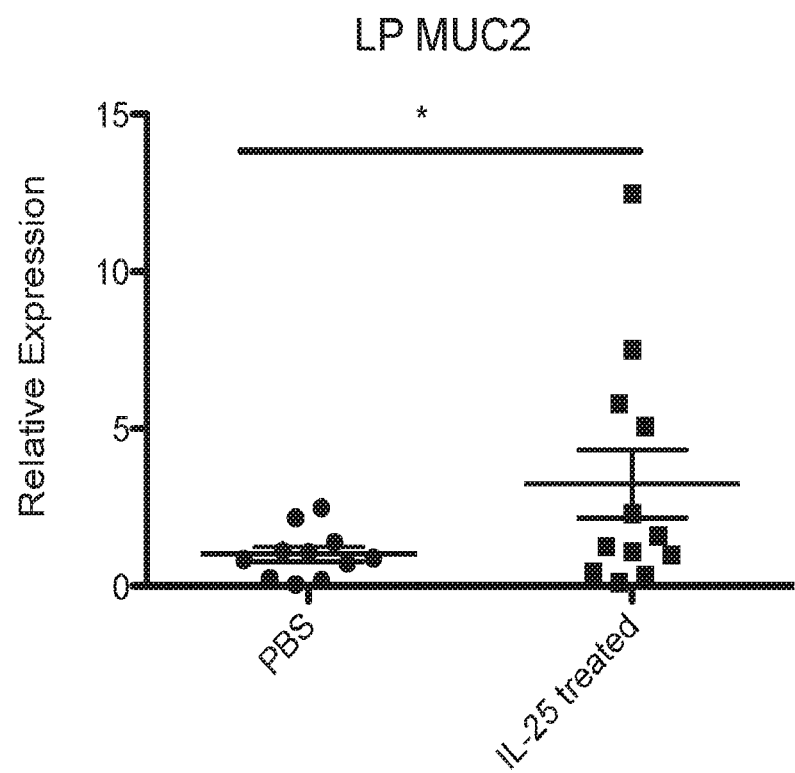
FIG. 9: MUC2 is increased in IL-25 treated mice.
Figure 10:
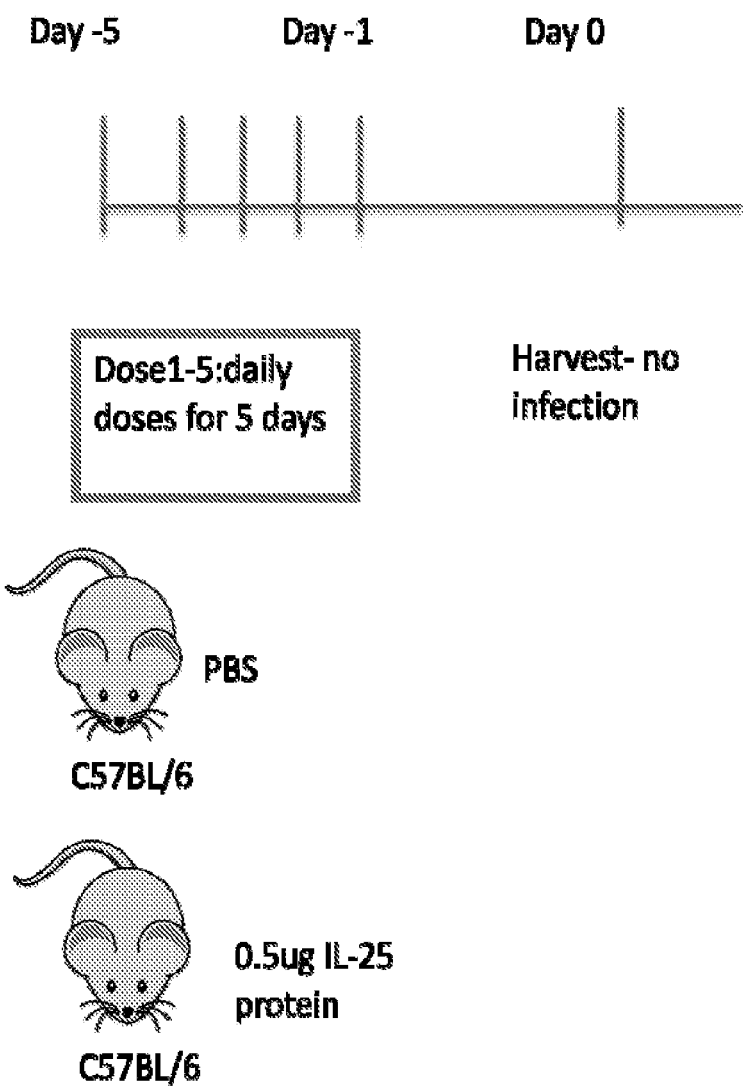
FIG. 10: How does Recombinant IL-25 Protein change the immune response?
Figure 12:
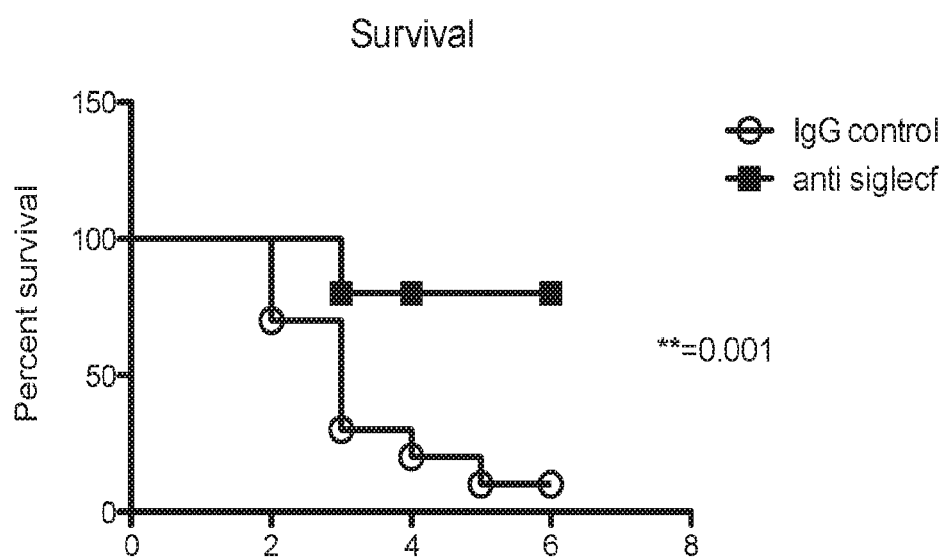
FIG. 12: IL-25 is not protective in the absence of Eosinophils. The graph illustrates that anti-siglecF, which reduces eosinophils, reduces survival in IL-25 treated and *C. difficile* infected mice.
Figure 13:
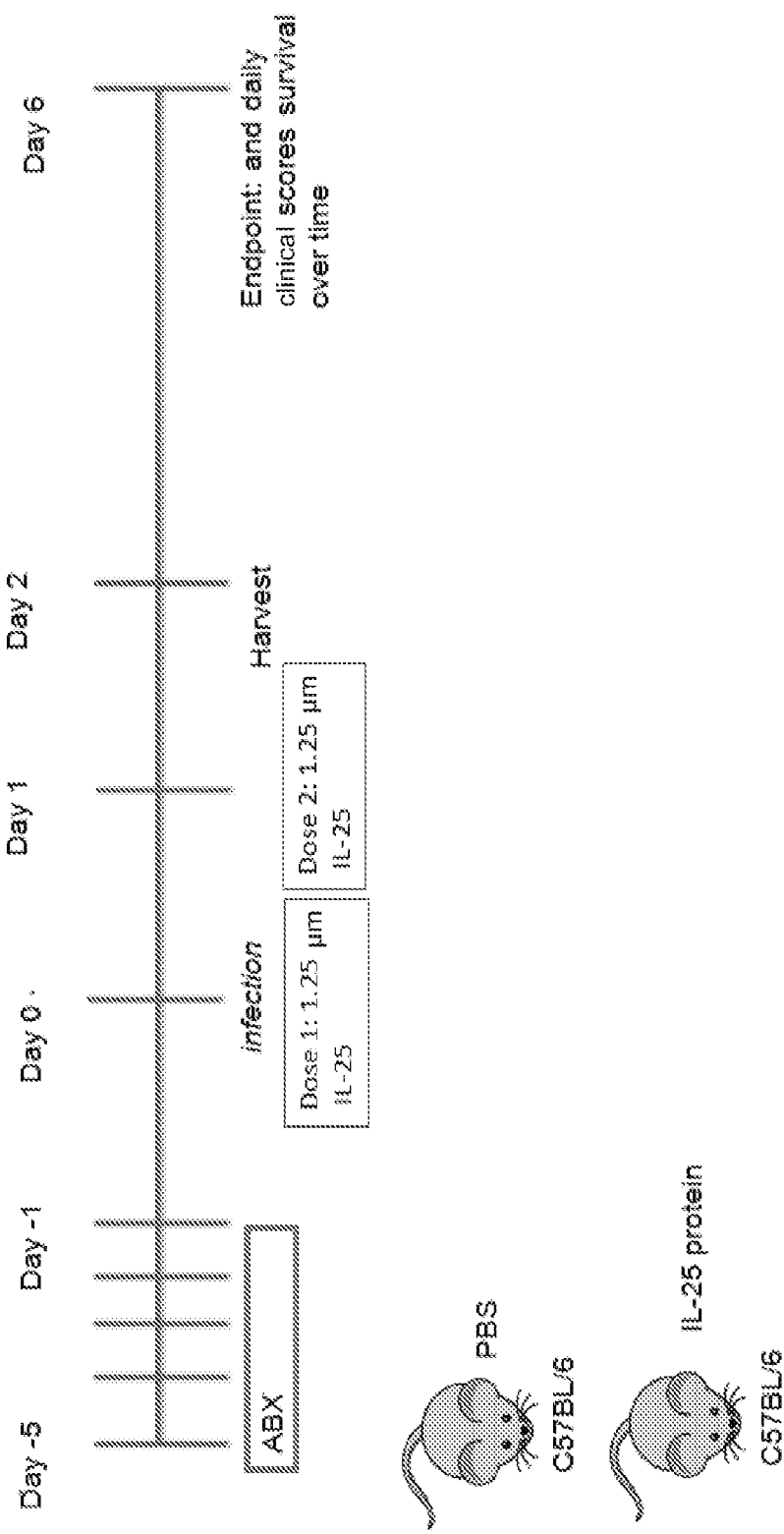
FIG. 13: Recombinant IL-25 Protein Assay Protocol. Schematic representation for a protocol of pretreatment with ABX from Days −5 to −1, infection on Day 0, and doses of IL-25 (1.25 µg) on Days 0 and 1, followed by harvest on Day 2. Endpoint at Day 6.
Figure 14:
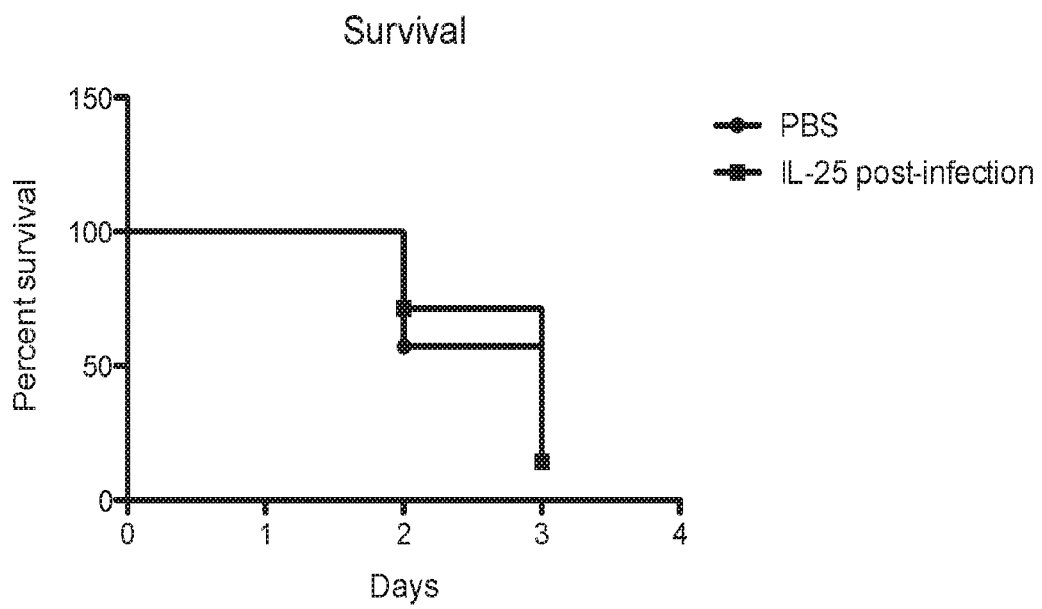
FIG. 14: Can restoration of IL-25 protect after infection?
Figure 15:
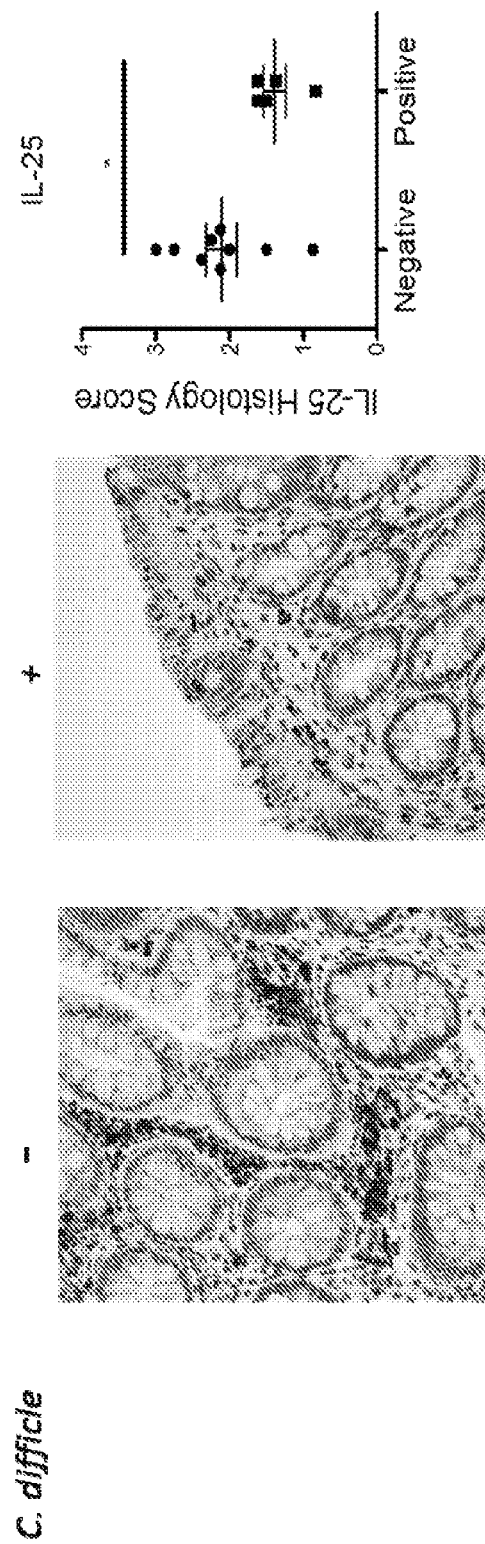
FIG. 15: IL-25 expression is decreased in the colons of *C. difficile* positive human subjects. Representative human colon biopsies were stained for IL-25 protein expression from *C. difficile* infection negative (left photomicrographic image) and positive (right photomicrographic image) patients. For the graphic (3rd panel) histologic sections were scored for abundance and intensity of IL-25 stain (expression) by four independent blinded scorers (n=5, n=9).
Figure 16:
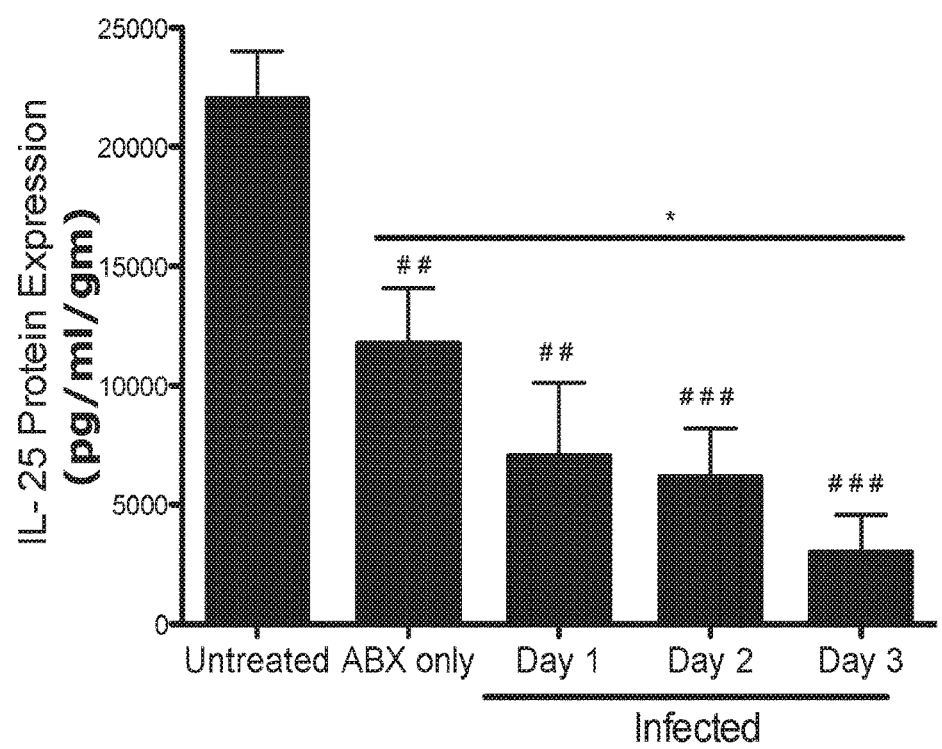
FIG. 16: Antibiotic (ABX) treatment and CDI both reduce IL-25 protein levels in mouse colons. IL-25 protein expression from colon tissue lysates of mice treated with only antibiotics or on day 1, 2, or 3 after infection were compared to untreated lysates (n=16). *<0.05, # indicates level of significance from untreated sample. Ordinate—IL-25 protein expression in pg/ml/gm); Abscissa—the five control and treated groups; the first two groups were not infected: Untreated (first bar); ABX only (second bar); Day 1 of infection (3rd bar); Day 2 of infection (fourth bar); and Day 3 of infection (bar 5). See also FIG. 32A-D demonstrating that IL-25 regulation can vary depending on the antibiotic used.
Figure 17:
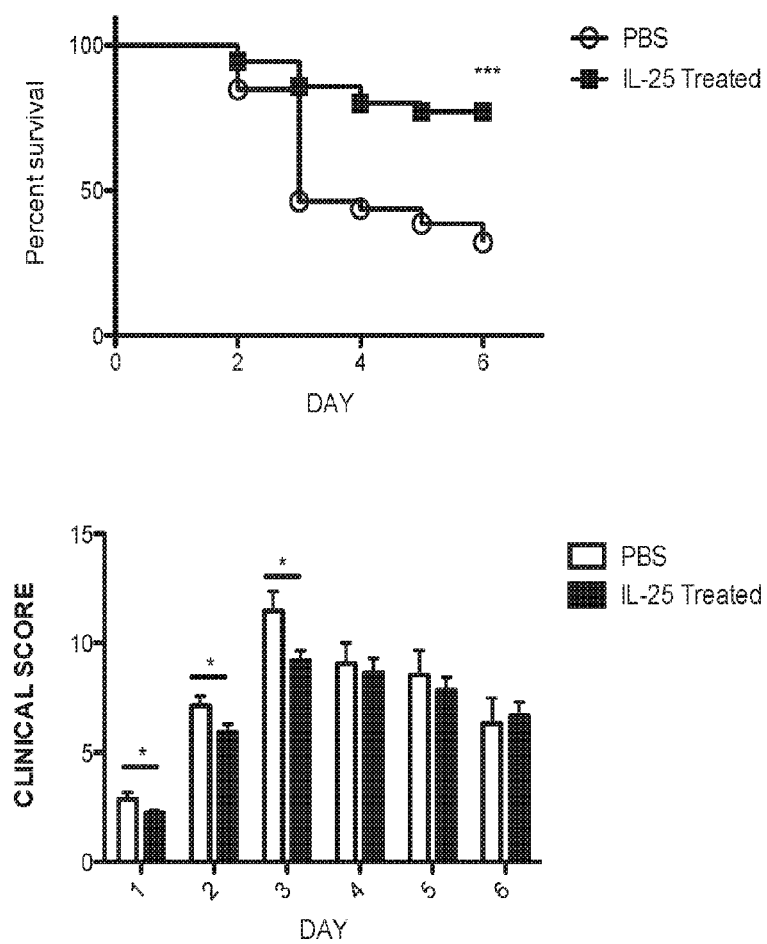
FIG. 17: Restoration of IL-25 signaling prior to infection protects mice from morbidity and mortality. Mice were pretreated with recombinant IL-25 protein daily for 5 days prior to infection and assessed for survival and morbidity (n=46, 46). IL-25 repletion led to increased survival (77%) when compared to control mice (32%). IL-25 pretreatment decreased clinical scores in early stages of infection. Upper Graph depicts percent survival through day 6 for PBS treated and for IL-25 treated. Lower Graph depicts clinical for days 1-6 for the PBS control and for IL-25 treated. Repletion of IL-25 in mice during antibiotic pre-treatment and during CDI (upper panel) increased survival and decreased morbidity.
Figure 19A:
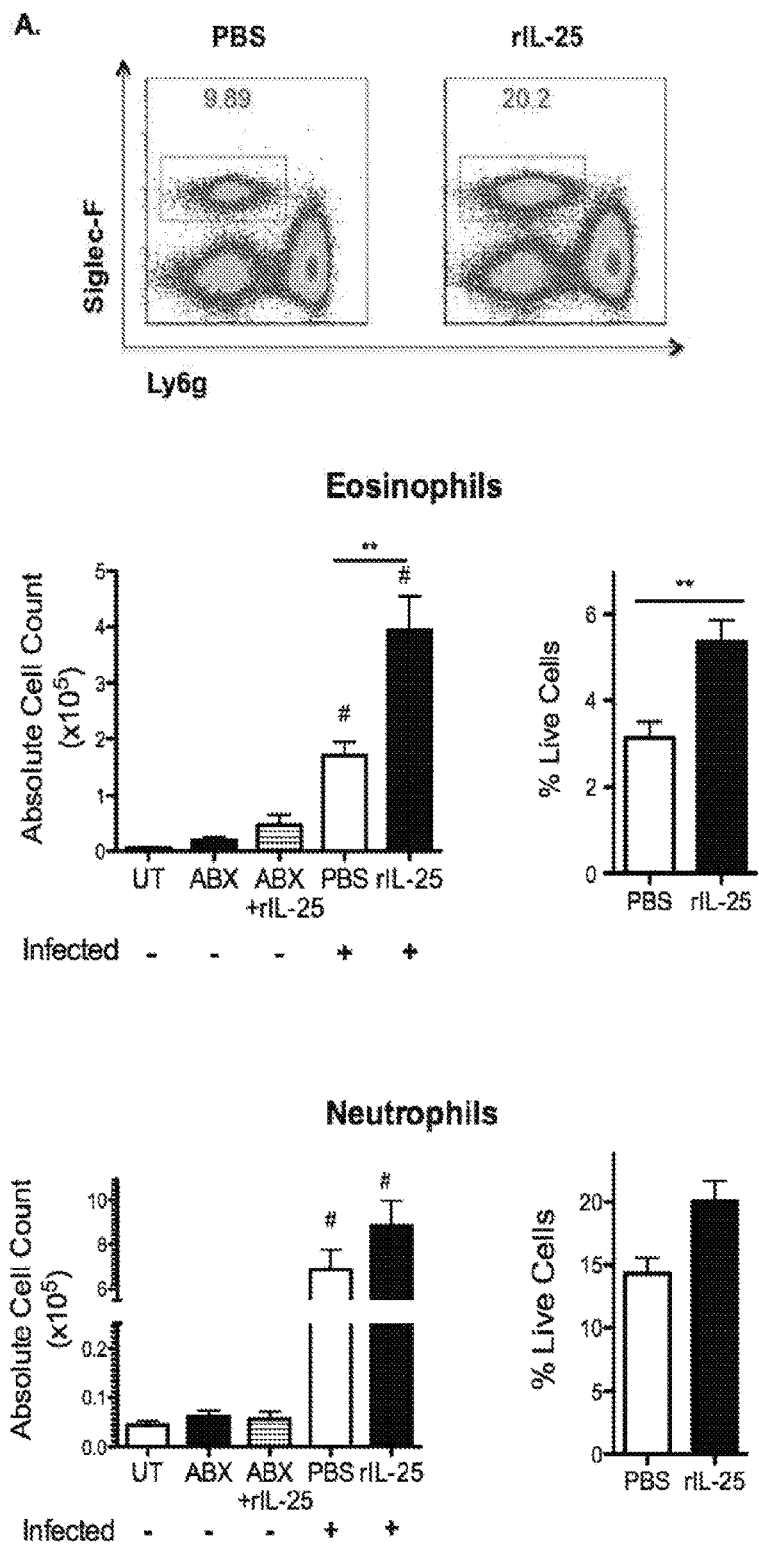
FIG. 19, comprising 19A-C, demonstrates that IL-25 induces eosinophilia and upregulates IL-4 and mucus production in the gut. Recombinant IL-25 treatment skews toward Th2-like responses on Day 3 post-infection. 19A, comprising 5 panels—IL-25 treated mice had enhanced accumulation of eosinophils, but not neutrophils, in the lamina propria of the colon compared to wildtype controls. 19B, comprising five panels—IL-25 treatment reduced levels of pathogenic IL-23 protein expression, but elevated IL-4 protein levels in the cecal tissue by ELISA. 19C, comprising two panels—IL-25 increased mucus as evidenced by enhanced MUC2 gene expression by qPCR analysis and Periodic-acid Schiff (PAS) staining, a method which allows for the visualization of mucin proteins. Colon tissue from PBS or rIL-25 treated mice was processed and recruitment of immune cells were analyzed on day 3 post-infection (n=12). Eosinophils are selectively increased with IL-25 treatment during CDI. Interestingly, IL-25 treatment does not influence the recruitment of neutrophils. This suggests that normal pro-inflammatory responses are maintained with IL-25 treatment to combat infection, but alternate pathways may be activated to enhance tissue repair.
Figure 19B:
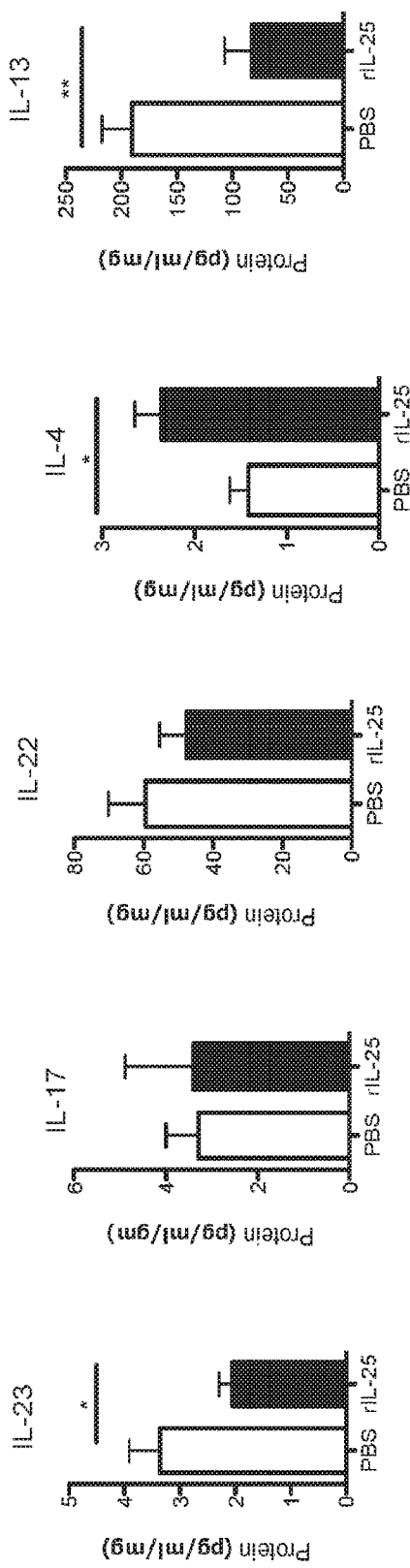
Figure 19C:
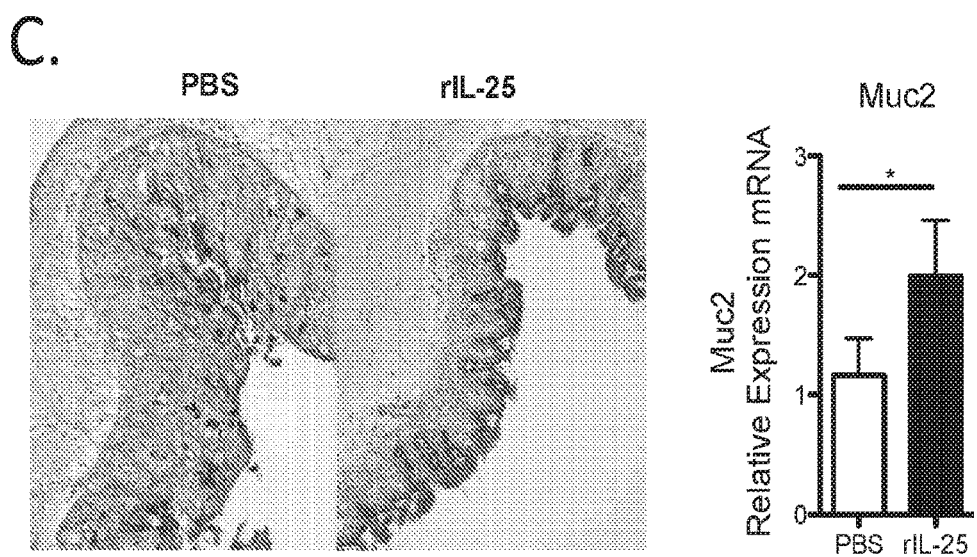
Figure 20:
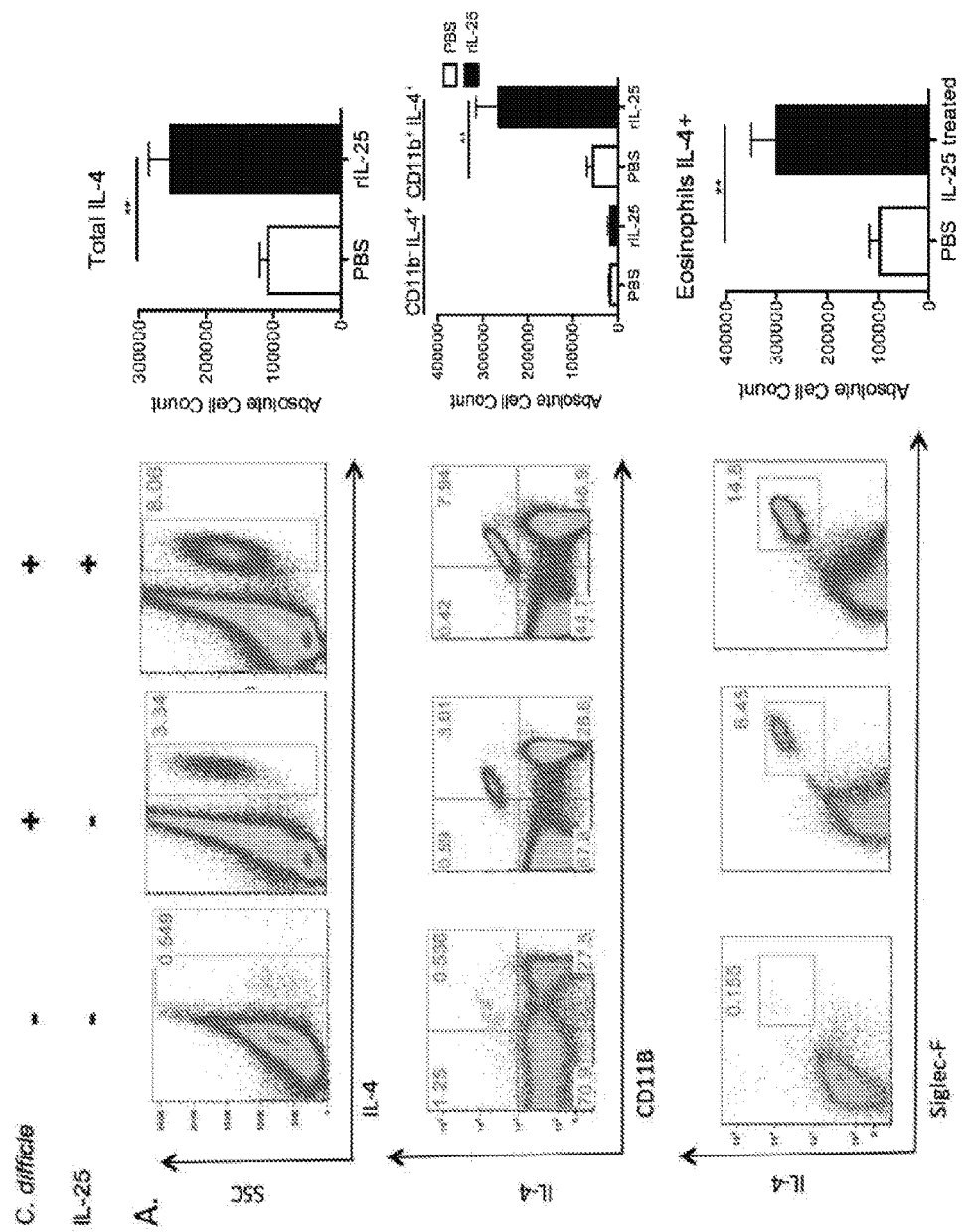
FIG. 20: IL-25 induces IL-4 production from eosinophils during *C. difficile* infection. Colon tissue cells from mice treated with PBS or IL-25 were processed and accessed for IL-4 production on day 3 post infection (n=6). IL-25 treatment induced higher overall IL-4 production during CDI. IL-4 production was primarily confined to CD11b+ cells indicating innate cells are responsible for the majority of signaling. Within the CD11b+ compartment, eosinophils were the major producers of IL-25-dependent IL-4 signaling. The left nine panels are protein level panels depicting expression of SSC vs IL-4 (upper three panels), IL-4 vs. CD11B (middle three panels), and IL-4 versus SiglecF (lower three panels) in uninfected controls with no IL-25 treatment, infected animals with and without treatment with IL-25. The three bar graphs on the right indicate PBS or IL-25 treated cell counts for Total IL-4 (upper graph) in terms of absolute cell count; either CD11b$^-$IL-4+ or CD11b+IL-4+ (middle graph); and Eosinophils IL-4+ (lower graph).
Figure 21:
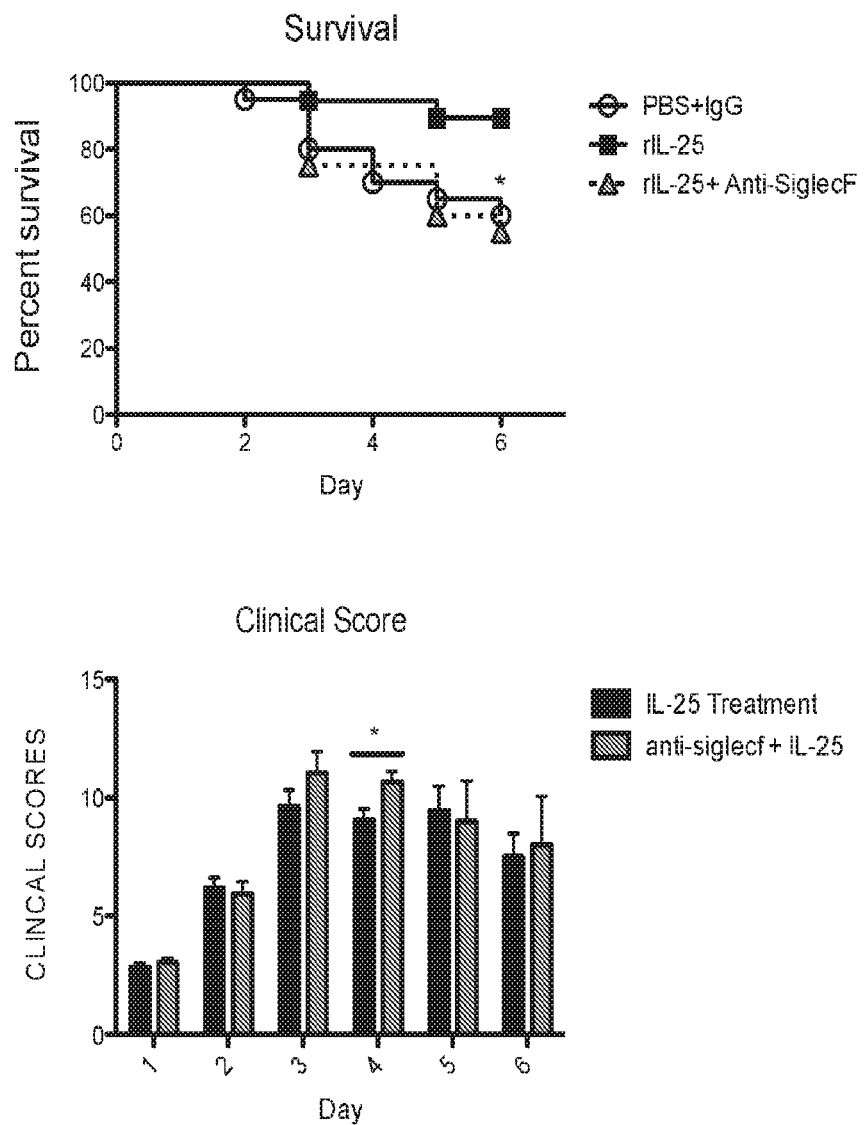
FIG. 21: Eosinophils are necessary for IL-25 mediated protection against CDI. The upper graph indicates percent survival for PBS+IgG treatment, rIL-25 treatment, and rIL-25+Anti-SiglecF treatment. The lower graph indicates clinical scores for days 1-6 for IL-25 treated and for Anti-SiglecF+IL-25 treated animals.
Figure 22:
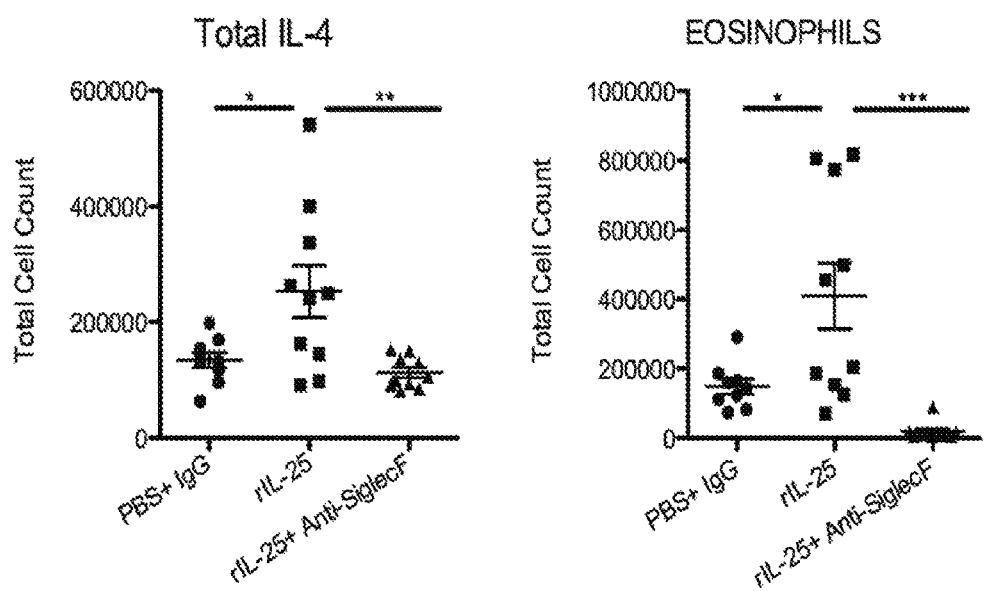
FIG. 22: Eosinophil depletion in IL-25 treated mice negates protection. Mortality and clinical scores are increased when eosinophils are depleted (n=20, 20, 20). IL-4 levels are reduced by flow cytometry in mice lacking eosinophils (n=12, 12, 12). Eosinophils are successfully depleted with antibody. The left graph represents Total IL-4 and the right graph represents Eosinophils. Treatments were—PBS+IgG, rIL-25, and rIL-25+Anti-SiglecF. Ordinate—total cell counts. IL-25 treated mice with anti-SiglecF neutralization have reduced (left graph) total IL-4 levels and total eosinophils (right graph) in the lamina propria on Day 3 post-infection by flow cytometry.
Figure 23:
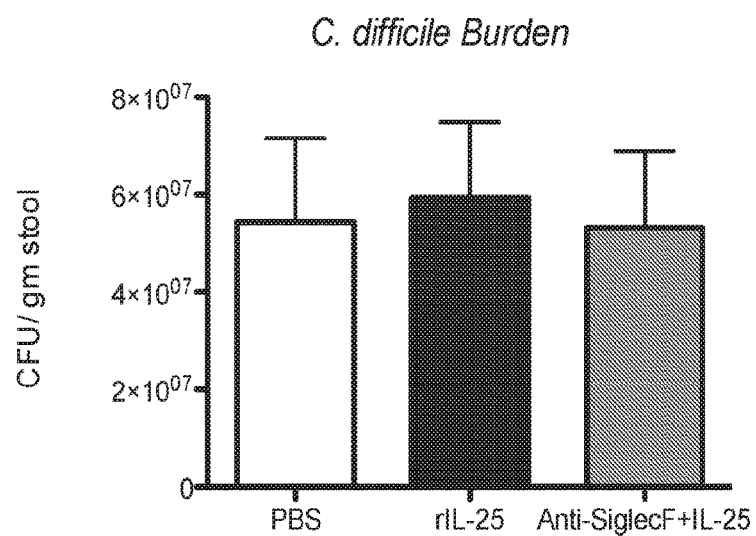
FIG. 23: Eosinophil depletion has no impact on *C. difficile* burden. *C. difficile* CFUs plated from stool on Day 3 post infection. Eosinophils do not play a role in controlling *C. difficile* bacterial burden (n=10, 10, 10). The figure graphically depicts *C. difficile* burden. Groups are: PBS, rIL-25, and Anti-SiglecF+IL-25. Ordinate—CFU/gm stool
Figure 24:
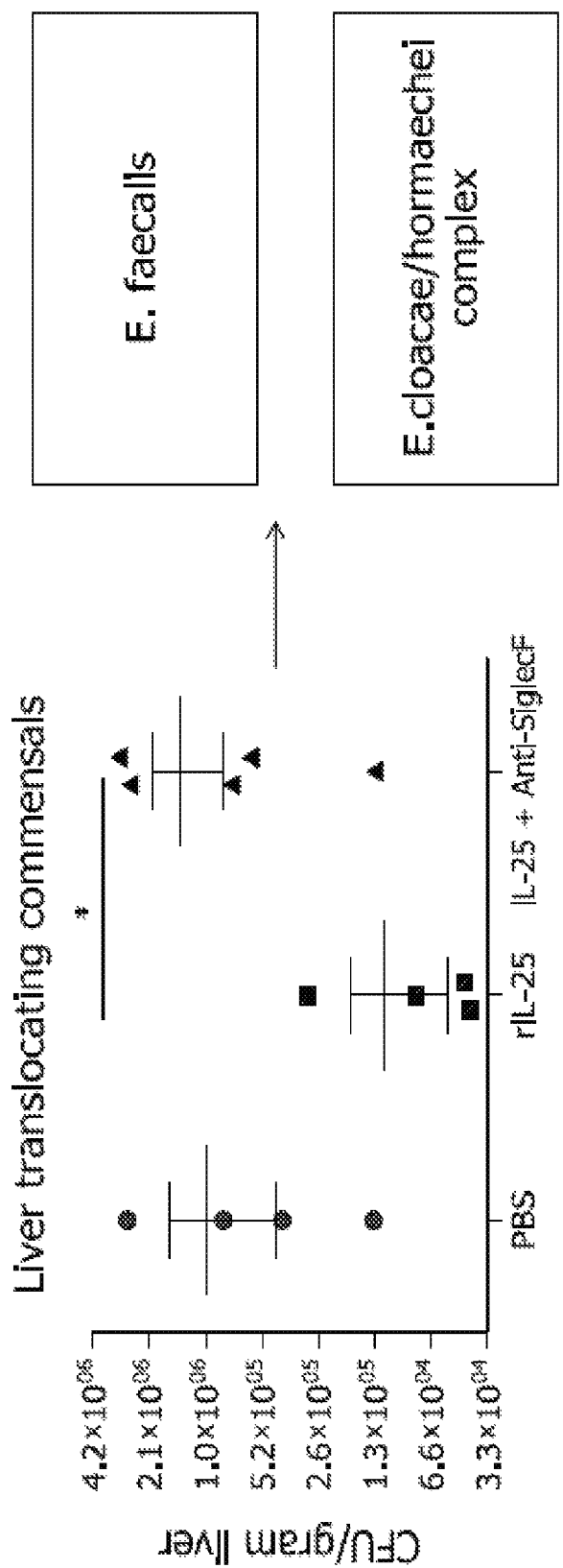
FIG. 24: IL-25 reduces bacterial translocation to the liver. Bacterial colonies plated from liver lysates on Day 3 post infection (n=5, 5, 5). DNA sequencing of bacterial colonies translocated to the liver in rIL-25+Anti-SiglecF treated mice. *E. faecalis* and *E. cloacae/hormaechei* are the major species isolated. Groups are: PBS, rIL-25, and Anti-SiglecF+IL-25
Figure 25:
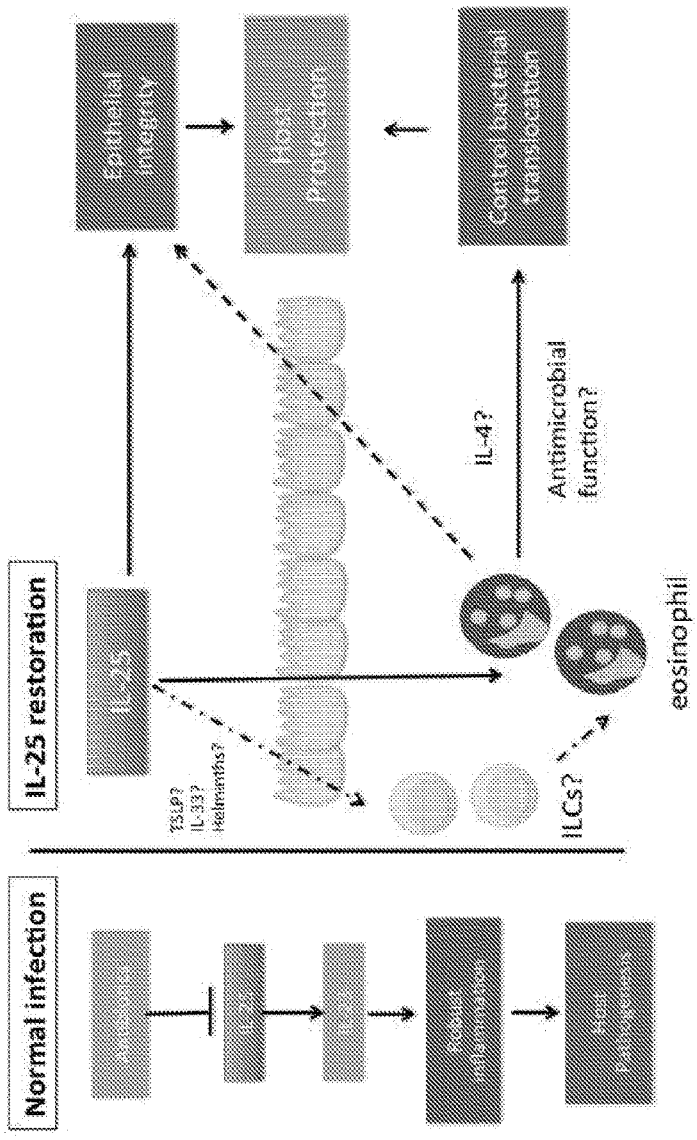
FIG. 25: Schematic Illustration depicting Normal Infection (left) and IL-25 Restoration pathways and interactions (right) and how IL-25 is downregulated during human and murine CDI. Repletion of IL-25 is protective against CDI-associated mortality. IL-25 induces IL-4 production from recruited eosinophils. Eosinophils are necessary for IL-25 dependent protection. IL-25/eosinophilia may protect via physical barriers and/or by its ability to inhibit bacterial translocation to the gut.
Figure 26:
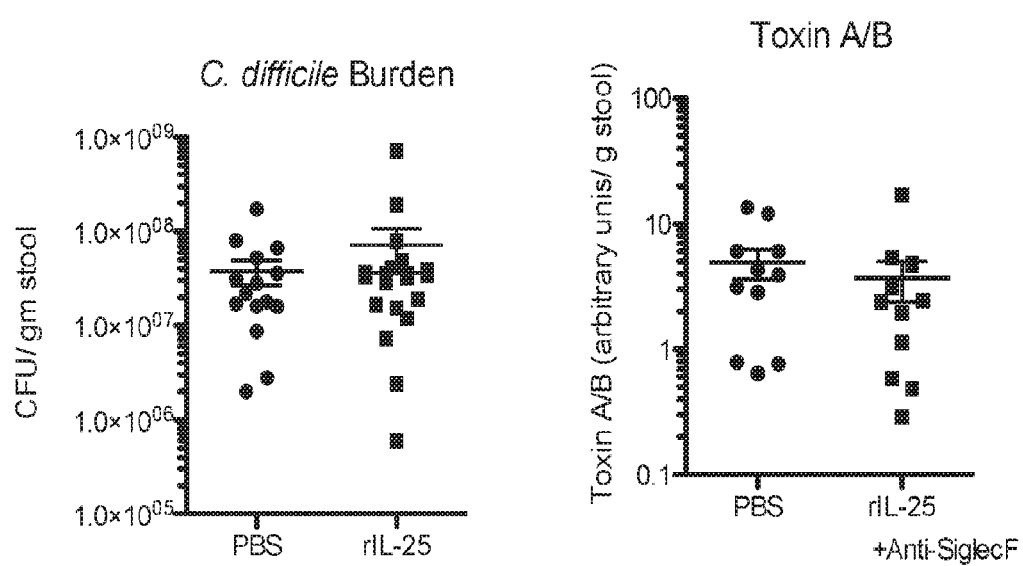
FIG. 26. IL-25 treatment does not alter the burden of *C. difficile*. The figure graphically depicts *C. difficile* burden after recombinant IL-25 treatment (left panel) and the Toxin A/B amount following IL-25+Anti-SiglecF treatment. IL-25 may protect through its influence on the immune response. PBS was the control for each.
Figure 27:
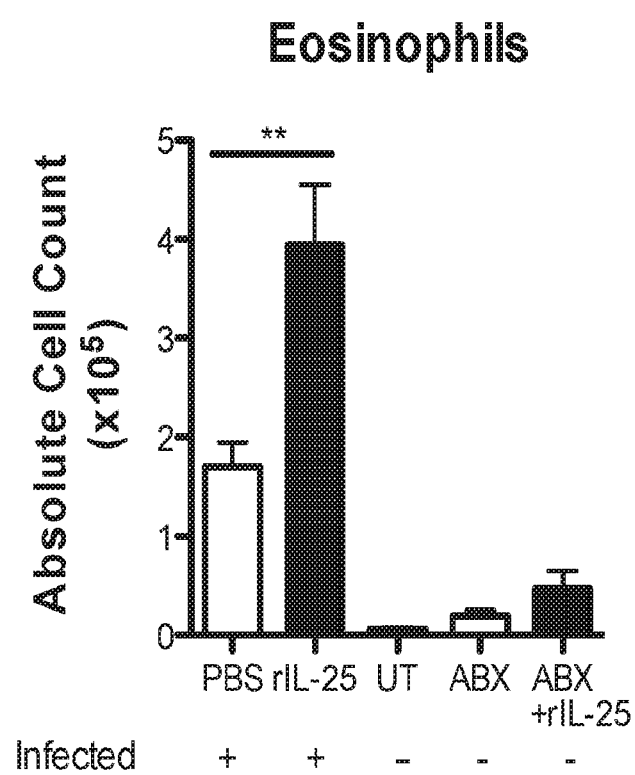
FIG. 27. IL-25 treatment increase eosinophils in colon lamina propria. The graph depicts the number of eosinophils in the colon of infected animals following PBS (control), rIL-25, UT, ABX, or ABX+rIL-25 treatment. The first two groups were infected. Lamina propria tissue from the colon at Day 3 of infection (n=15, n=17). Total counts and frequency of eosinophils are significantly increased with IL-25 treatment during infection.
Figure 28:
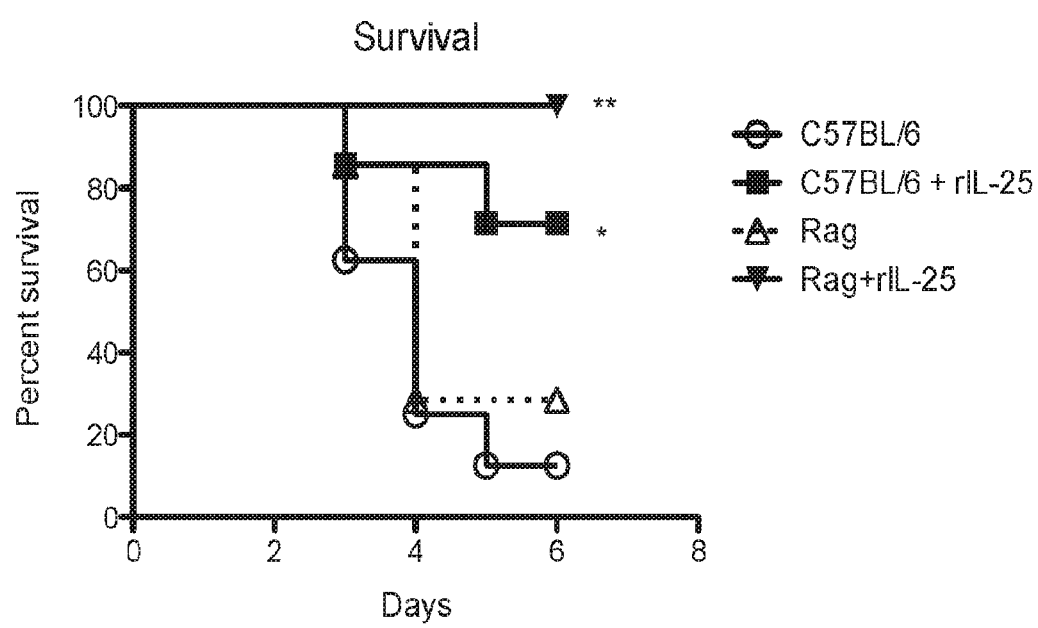
FIG. 28. IL-25 does not require adaptive immunity to protect against *C. difficile*. The figure is a depiction of survival (%) of infected animals (C57BL/6 and Rag) without treatment or treatment with rIL-25. Mice were treated with either PBS or 0.5 ug of recombinant IL-25. Rag mice, which lack T and B cells, were protected with IL-25 treatment to similar levels of WT mice indicating that the adaptive immune response is dispensable for IL-25 mediated protection. Rag$^{-/-}$ mice are protected from CDI with rIL-25 treatment. Adaptive response is not required for IL-25 to provide protection.
Figure 29:
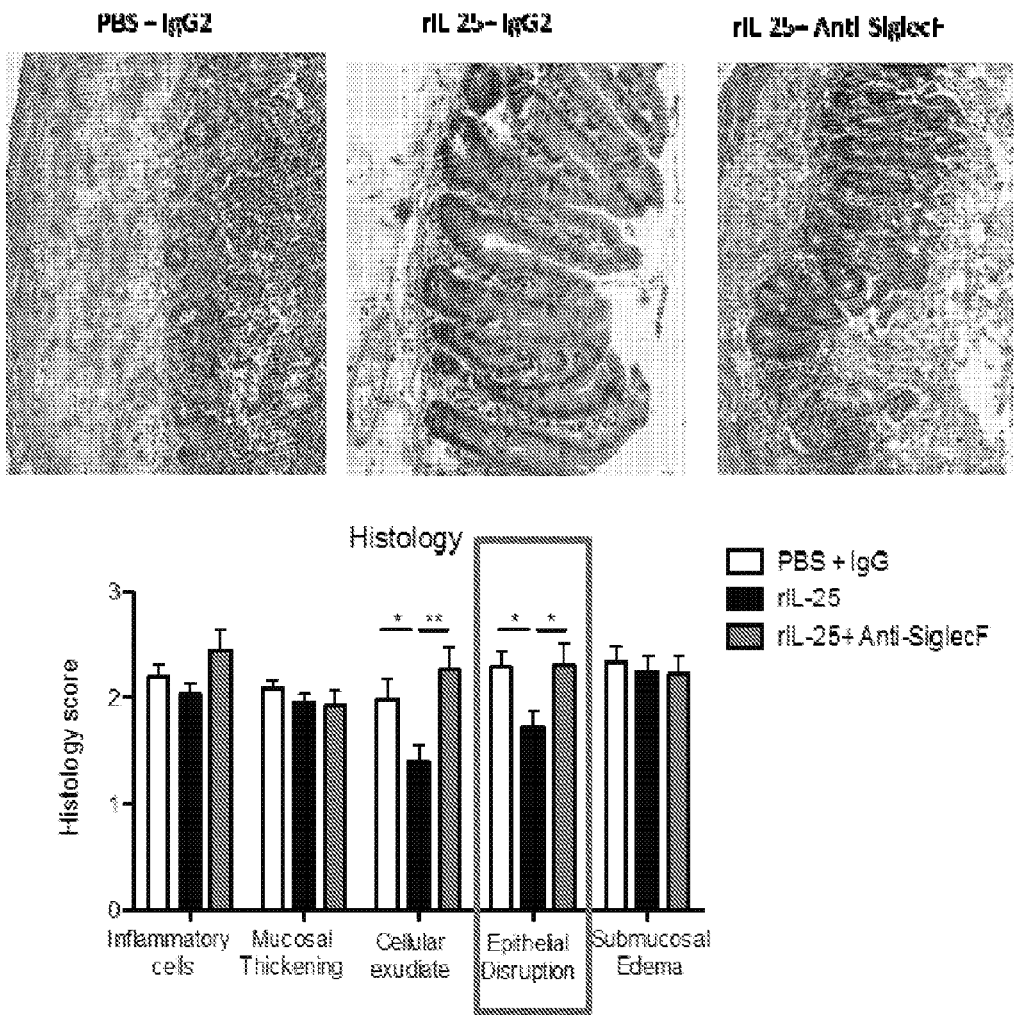
FIG. 29. Eosinophil depletion leads to increased epithelial disruption. The upper three panels are photomicrographs of animals treated with PBS+IgG$_2$, rIL-25+IgG$_2$, or rIL-25+Anti-SiglecF. The lower panel/graph indicates histology scores for inflammatory cell, mucosal thickening, cellular exudate, epithelial disruption (highlighted with a box), and submucosal edema.
Figure 30:
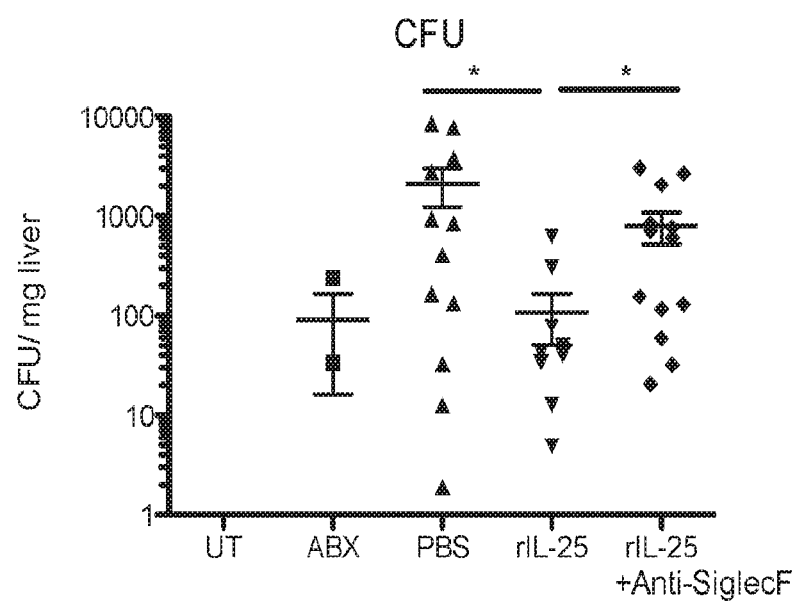
FIG. 30. Eosinophils may provide protection by controlling commensal translocation. The graph indicates, day 3 post infection the CFU in the liver, based on the following: UT, ABX, PBS, rIL-25, and rIL-25+anti-siglecF.
Figure 31:
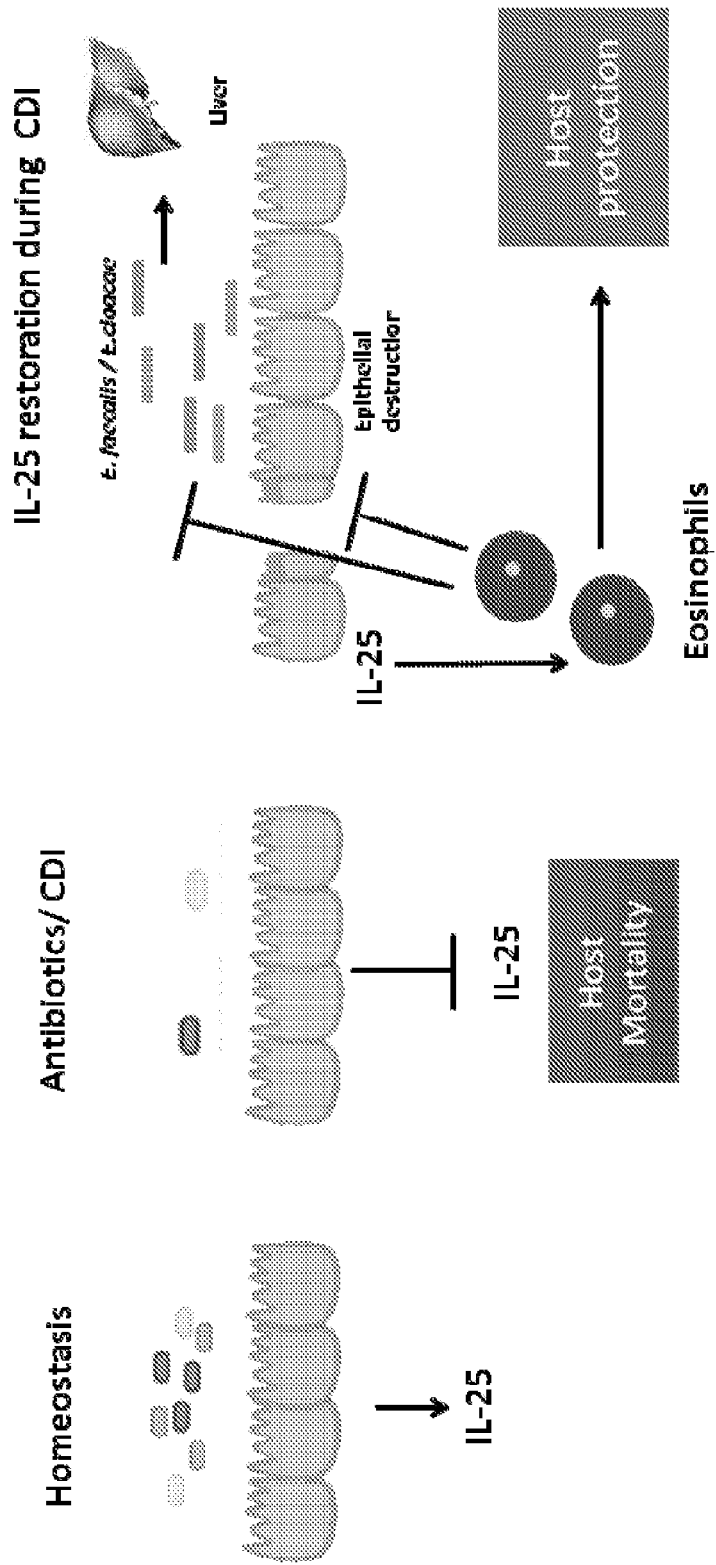
FIG. 31. Microbiota induced IL-25 signaling is protective during *C. difficile* infection. The figure is a schematic representation of Homeostasis, Antibiotics/CDI effect on host mortality, and IL-25 restoration and host protections during CDI as disclosed herein.
Figure 32A:
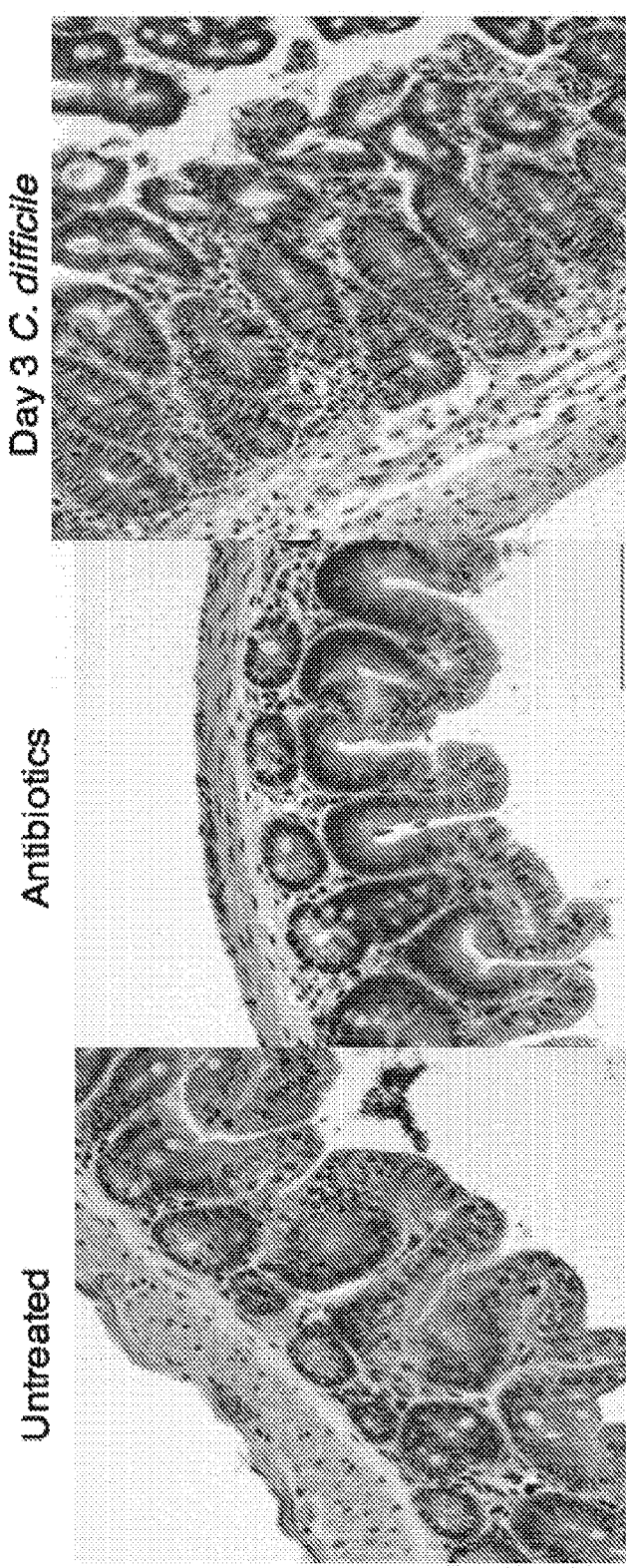
FIG. 32, comprising FIGS. 32A-D, demonstrates the effects of various antibiotics on IL-25 expression in the intestine: Epithelial IL-25 expression is reduced by antibiotics and CDI in mice. IL-25 was decreased with antibiotics and on Day 3 of CDI in mice by both (32A) histology (32B) and protein levels. The main source of IL-25 protein was in the epithelial layer (32C). Treatment with a single antibiotic (left panel, 32D) demonstrated that clindamycin significantly reduces IL-25 while metronidazole significantly increases IL-25 expression (right panel, 32D). *<0.05 and #<0.05, ##<0.01, ###<0.005. 32A—left micrograph (untreated), middle micrograph (antibiotic treated), and right micrograph (Day 3 *C. difficile*); 32B—graphic illustration of mouse IL-25 expression in untreated, antibiotic only, and days 1, 2, and 3 of infection. 32C—graphical illustration of IL-25 expression in the lamina propria and in the epithelium. 32D, comprising left and right panels, graphically illustrates IL-25 expression: 32D, left panel, depicts epithelial IL-25 expression in groups with no antibiotics (No Abx), antibiotics only (Abx only), and infected mice. 32D, right panel, graphically illustrates IL-25 expression in colon tissue for animals treated with nothing (Untreated), All Antibiotics, Metronidazole, Vancomycin, Gentamycin, and Clindamycin. For the groups listed here, mice were treated with one of the antibiotics and cecal tissue levels of IL-25 protein was measured by ELISA. Metronidazole, Vancomycin, and Gentamicin were given in the drinking water for 3 days and a single dose of Clindamycin was injected intraperitoneally. Treatment with a single antibiotic demonstrated that clindamycin alone significantly reduces IL-25, while metronidazole significantly increases IL-25 expression.
Figure 32B:
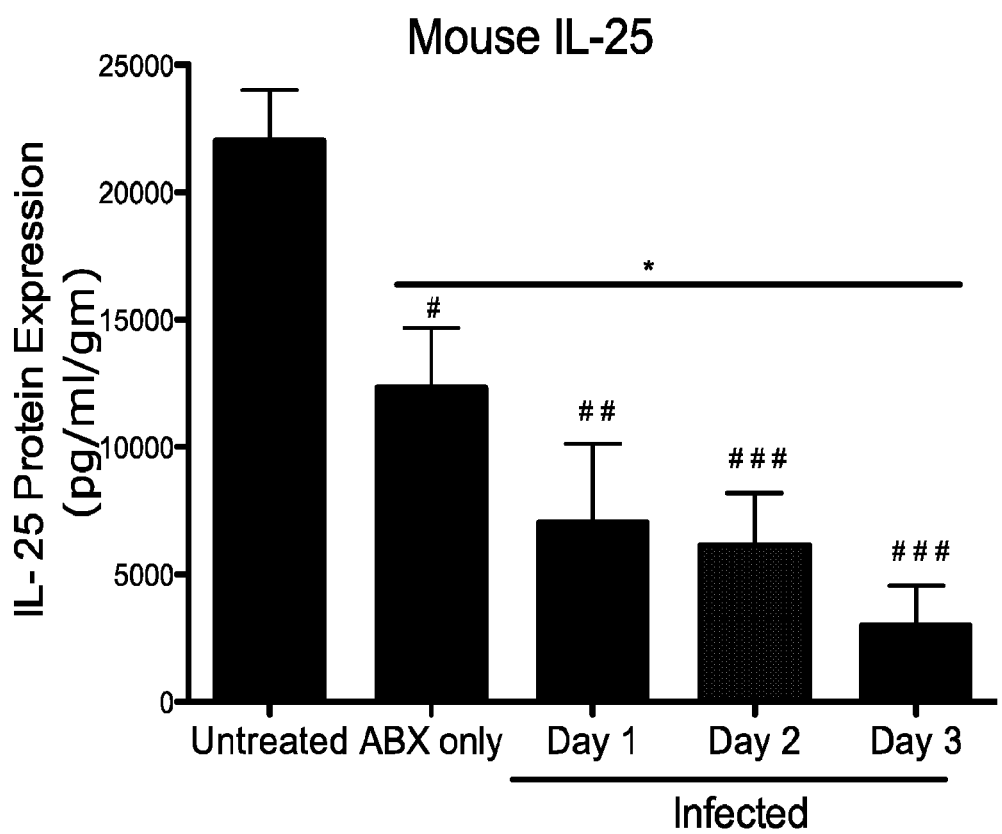
Figure 32C:
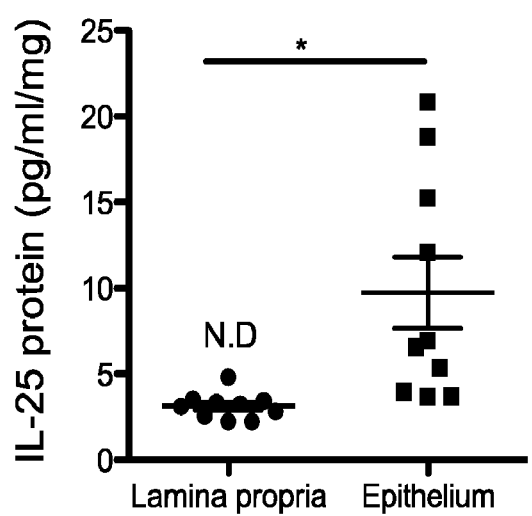
Figure 32D:
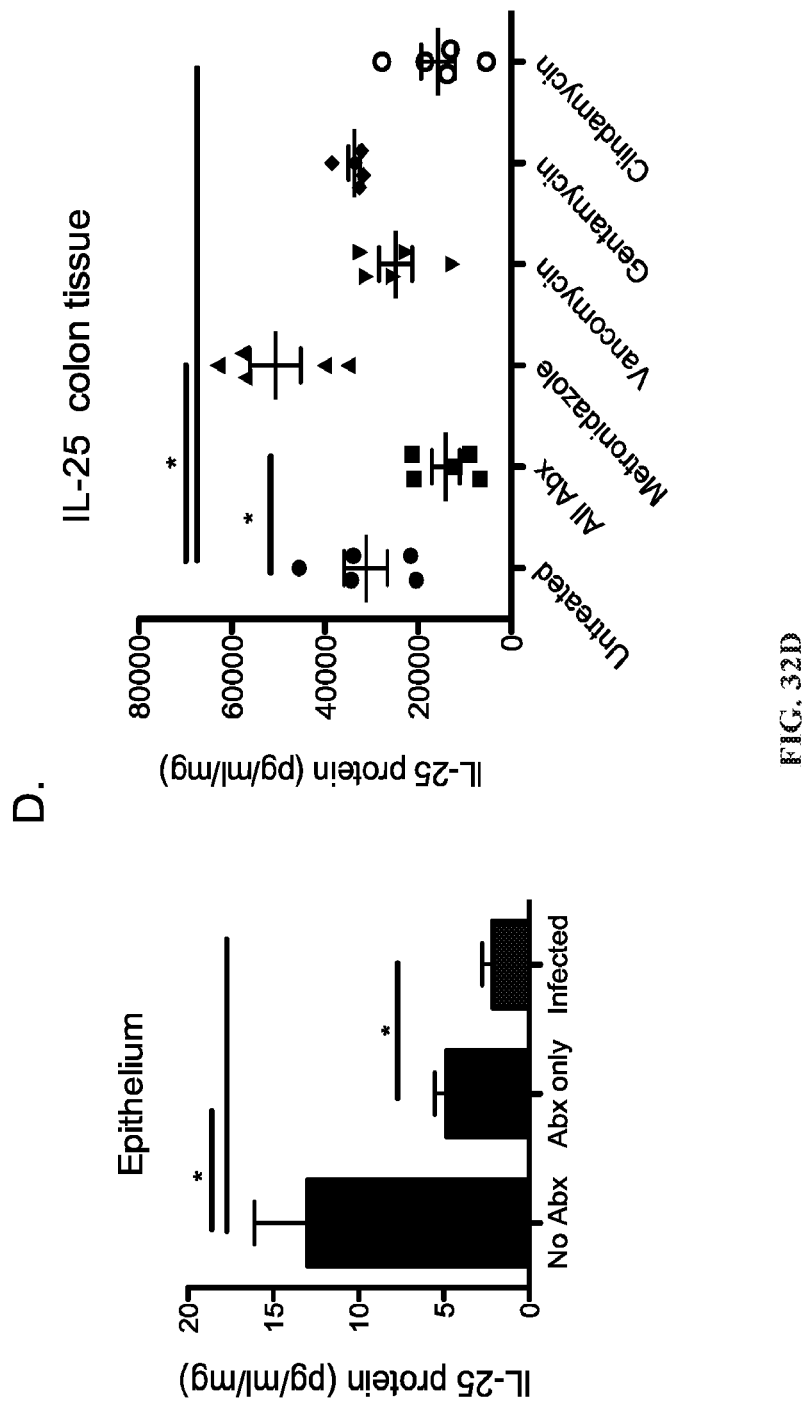
Figure 33:
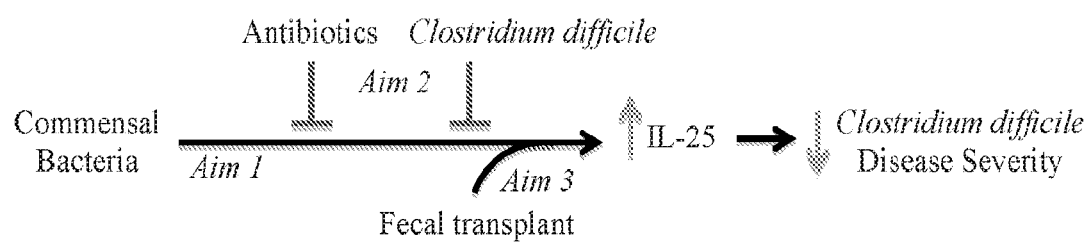
FIG. 33. Schematic representation of the steps and method for the use of commensal bacteria, fecal transplants, and the role of antibiotics in treating and preventing *C. difficile* infection.
Figure 34:
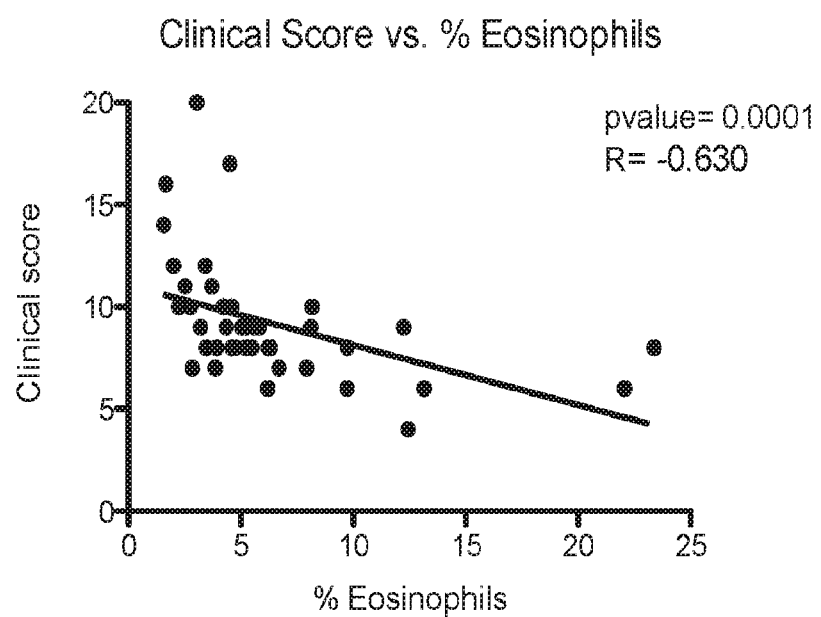
FIG. 34. Eosinophils correlate with reduced CDI-associated morbidity in mice. Mice with increased clinical scores have a significant correlation with reduced percentages of eosinophils in the lamina propria of the colon on Day 3 post infection.
Figure 35:
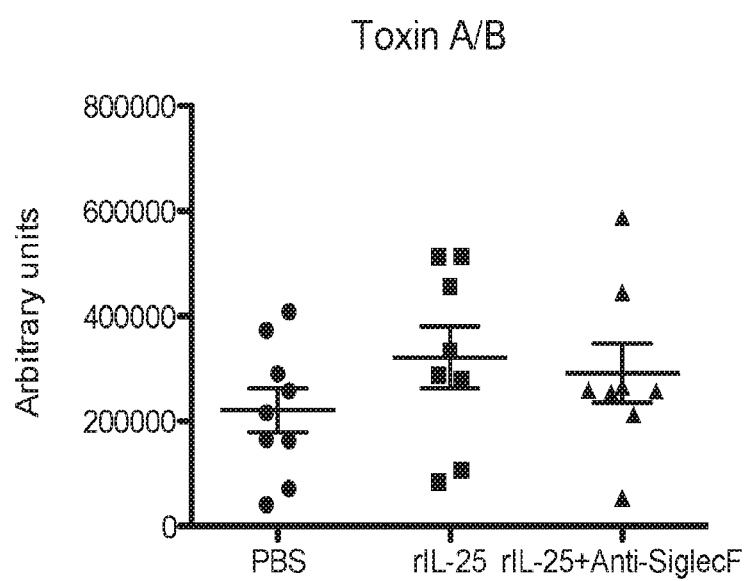
FIG. 35. Eosinophils are essential for IL-25-mediated protection. Mice were treated with PBS, rIL-25, or rIL-25+Anti-SiglecF. *C. difficile* burden was assessed. Anti-SiglecF antibody depletes eosinophils and 20 ug was given on Day −1 and Day 1 of infection. IL-25+Anti-SiglecF mice had enhanced mortality and morbidity when compared to IL-25 treated mice (see other figures). Depletion of eosinophils did not influence *C. difficile* burden (see other figures) or toxins A and B in the stool. Depletion of eosinophils does not influence toxins A and B in the stool.
Figure 36:
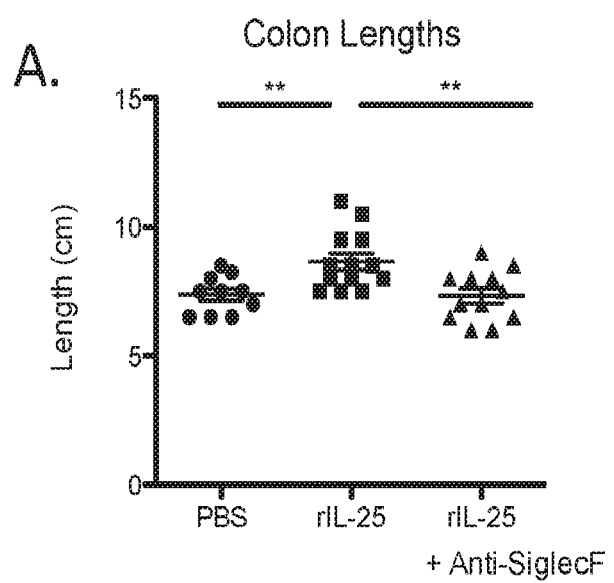
FIG. 36, comprising 36A-D, demonstrates that Eosinophils are necessary for IL-25 dependent intestinal epithelial barrier protection. Eosinophil depletion via anti-siglecF neutralizing antibody negates IL-25 mediated protection of the barrier by: (36A) reducing colon length indicating more severe colitis, (36B) enhancing epithelial destruction at the intestinal barrier and (36C) translocation of microbial pathobionts such as *E. faecalis* and *E. cloacae* to the liver. (36D) Upregulation of Aspartate transaminase (AST) in the serum of rIL-25-anti-siglecf on Day 3 post infection indicates elevated organ failure.
Figure 36B:
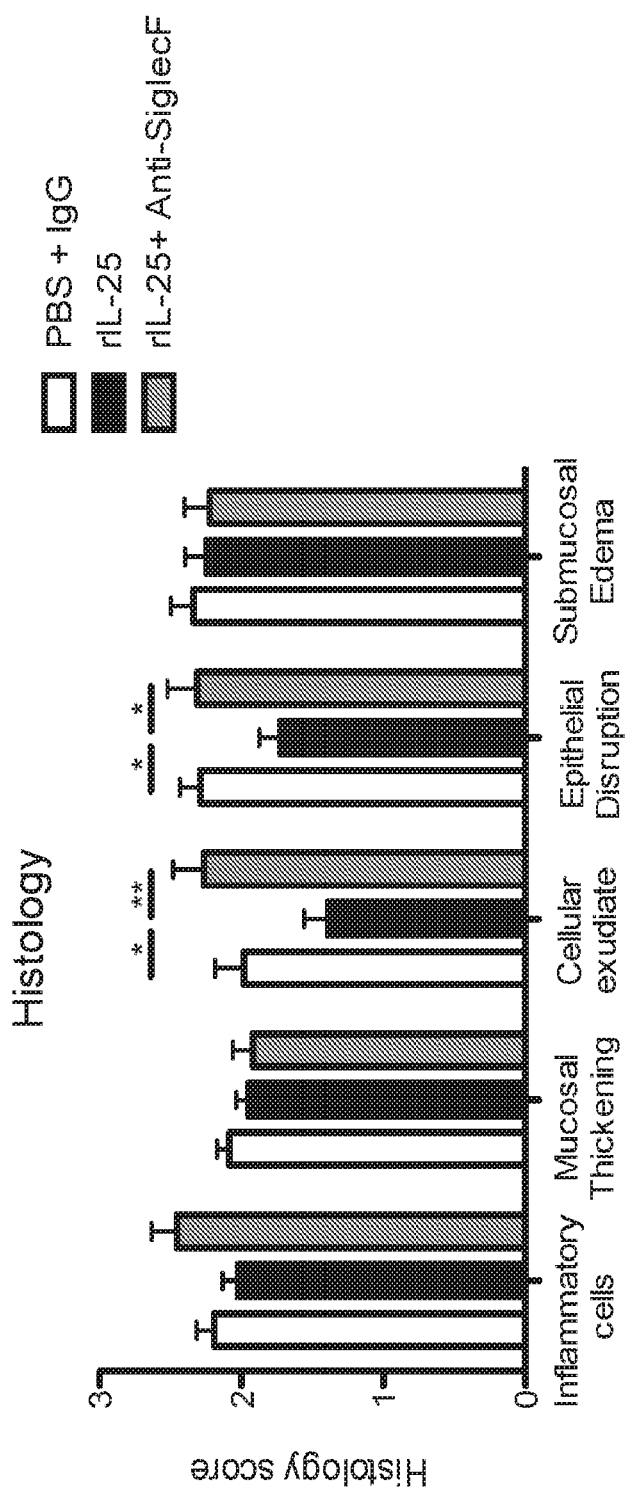
Figure 36C:
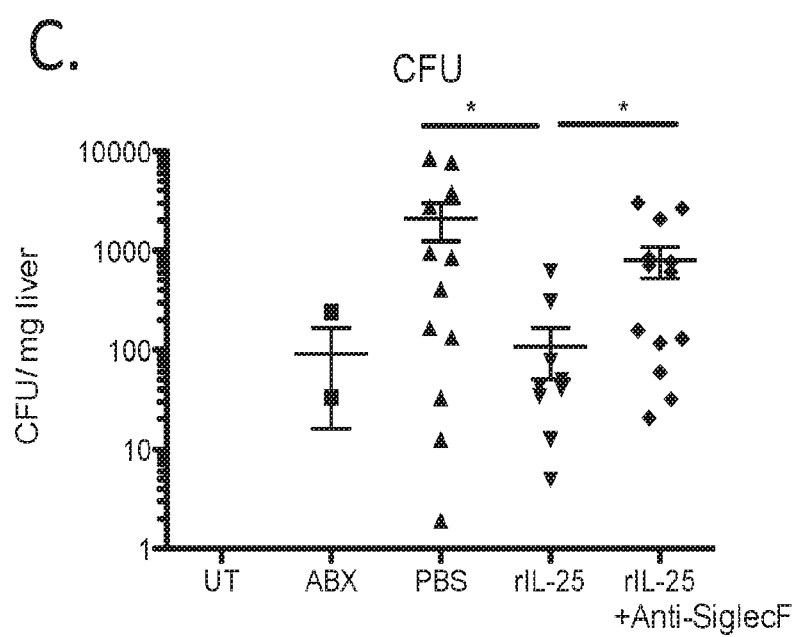
Figure 36D:
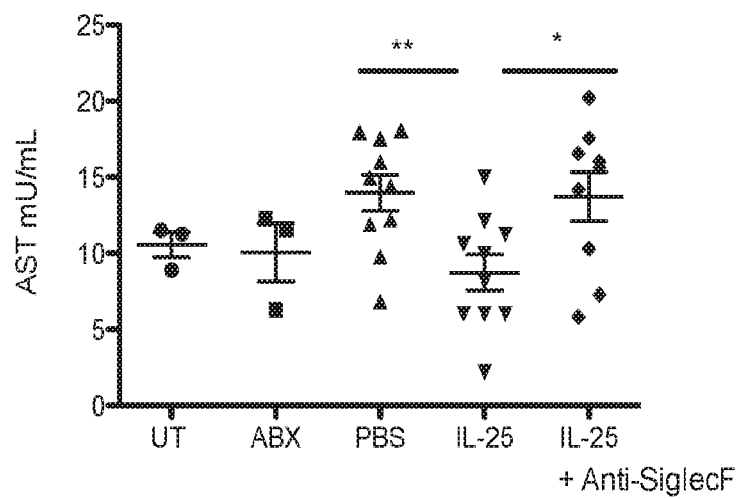

Th2-immune responses are characterized by the cytokine milieu (IL-4, IL-5, and IL-13) as well as the recruitment of eosinophils, basophils, and mast cells. Our data indicate that eosinophils are increased during IL-25 treatment (FIG. 3). Interestingly, eosinophils are also the main producers of IL-4 during CDI and IL-25 treatment significantly increases IL-4 expression from these cells (FIG. 4). Additionally, IL-25 treatment results in enhanced production of anti-inflammatory mediators IL-10 and mucin (MUC2) (FIGS. 5-6).

It is also Shown that IL-25 Decreases Upon Antibiotic Treatment and in Animals with CDI Without wishing to be bound by any particular theory it is hypothesized herein that IL-25 provides protection by promoting a balance between pro-inflammatory and tissue repair processes. Thus, an inflammatory response is induced to clear bacteria but does not disrupt epithelial cell integrity by also enhancing tissue repair mechanisms. This balance in the immune response created by IL-25 signaling functions to protect the host during CDI.

Inappropriate inflammation during *Clostridium difficile* infection (CDI) is implicated in pathogenesis. Our goal is to determine immune mediators that promote healthy inflammation. We hypothesize that IL-25 is protective by providing necessary signals to maintain balance between harmful inflammation and tissue repair during CDI. We have found that treatment of mice with recombinant IL-25 resulted in 75.9% survival compared to 31.6% survival seen in controls (p=0.002). IL-25 treatment during CDI is associated with the upregulation of anti-inflammatory mediators, such as IL-10 (p=0.03) and Mucin (MUC2) (p=0.02), but surprisingly mice maintain comparable levels of neutrophil recruitment. Treatment with IL-25 also enhances the recruitment of eosinophils to the gut (p=0.002) and the ability of eosinophils to produce IL-4 (p=0.04). We propose that IL-25 is pivotal in protecting tissue integrity by supporting anti-inflammatory and repair signals to counteract pathogenic inflammation normally seen in CDI. Next, we aim to elucidate the mechanisms by which IL-25 provides protection.

The Pathologic Innate Response to *C. Difficile* Infection Suppresses IL-25 in the Mouse Model and in Humans with CDI.

Experiments were performed in which the epithelial and lamina propria layers were separated and it was revealed that the primary source of IL-25 protein is in the intestinal epithelium.

Interestingly, using single antibiotic treatments we established that clindamycin was the only antibiotic that could deplete IL-25 levels similarly to the multiple antibiotics utilized in the murine model of CDI, while single treatments with metronidazole significantly elevated IL-25 levels from untreated mice (see figures). Other antibiotics tested were vancomycin and gentamycin. In these experiments mice were treated with a single antibiotic and cecal tissue levels of IL-25 protein were determined using ELISA.

Additionally, the data show that IL-25 protein is reduced in infected mice and humans. Colon biopsies from human subjects testing positive for CDI had significant reductions in IL-25 expression.

IL-25 protected from CDI colitis in mice: IL-25 was administered for five days prior to infection with *C. difficile*. Mice receiving IL-25 were protected from lethal CDI (see figures). Interestingly, IL-25 treatment did not change bacterial burden, but decreased epithelial disruption at the intestinal barrier. IL-25 mice displayed decreased IL-23 expression (data not shown) which was of interest because we had earlier demonstrated that IL-23 signaling is pathogenic in a mouse model of CDI. We conclude that IL-25 is protective in the murine model of CDI.

Gut eosinophils are increased by IL-25 and are the major source of IL-4: IL-25 signaling is known to promote Th2-like immune skewing characterized by eosinophil recruitment, activation of tissue repair pathways, goblet cell hyperplasia, and mucus production. We therefore tested if mice treated with IL-25 had greater numbers of eosinophils. Treatment with IL-25 increased the number of eosinophils in the gut (see figures). Furthermore, the data show that eosinophils were the major source of IL-4 in the gut as determined by intracellular cytokine staining. IL-25 administration also increased mucus (Muc2) expression in the colon (data not shown). We concluded that IL-25 increased gut eosinophils and Muc2.

Eosinophil depletion blocked IL-25 protection: To further understand the role of eosinophils, experiments were performed to determine what would happen if eosinophils were depleted. Eosinophils were depleted via administration of anti-siglecF monoclonal antibody 18 hours prior to infection and then 1 day post infection. Depletion of eosinophils abrogated IL-25 mediated protection from death due to CDI colitis, decreased eosinophil numbers and IL-4 in the gut, and increased bacterial translocation. It is hypothesized herein that eosinophilia may function to protect against CDI by activating tissue repair pathways via IL-4 and/or enhancement of intestinal barrier protection through increased mucus production. We conclude from the data that IL-25 protected from death due to CDI by increasing the numbers of IL-4 producing eosinophils in the gut. It is concluded that CdtB increased lethality was not due to an increased bacterial burden but was associated with inflammation and a decrease in gut eosinophils.

The data further show that there is a correlation between IL-25 and protection from CDI and for effectiveness in treating CDI. Additionally, the data show a direct role for eosinophils (a loss of eosinophils resulted in a loss of IL-25 protection) and that the levels of eosinophils can be important for successful treatment and diagnosis.

Without wishing to bound by any particular theory, based on the data disclosed herein, it is hypothesized that innate protection from CDI is mediated by gut microbiota induced intestinal epithelial cell production of IL-25. We further hypothesize that dysbiosis induced by antibiotics and by CDI inhibits IL-25, rendering mice susceptible.

The data show a correlation and interaction of several factors related to suppression of IL-25, antibiotic-induced changes in commensal bacteria, the role of eosinophils, and the microbiota in preventing and treating CDI. The links disclosed herein suggest that a specific bacterium or combination of bacterium is responsible/useful for inducing IL-25 production in intestinal epithelial cells.

See also FIGS. 1 to 36A-D and the Tables Below.

Discussion

*Clostridium difficile* is an anaerobic bacterium that causes antibiotic-associated colitis and diarrhea. It is a leading cause of hospital-acquired infections, recently surpassing methicillin resistant *Staphylococcus aureus* MRSA in frequency.[1] It is postulated that disease severity is correlated with the intensity of host inflammatory response. Therefore, a better understanding of the mechanisms by which *C. difficile* causes pathology is necessary to develop therapies that modulate the host inflammatory response as a novel way to treat disease.

Administration of IL-25 in the treatment or prevention of CDI is a host-based therapy and the first target in the Th2 pathway implicated to benefit patients with CDI.

There is a need for a non-antibiotic treatment during *C. difficile* infection as depicted by a current 15% 30-day mortality rate. Antibiotic treatment further disruptions natural gut flora eliminating its potential protective capacity against infection. Current treatments also lead to the evolution of hyper virulent strains. Our host-based therapy circumvents these disadvantages.

*Clostridium difficile* is currently the leading cause of nosocomial infections in the United States, resulting in approximately 14,000 deaths per year and costing the US health care system an estimated $4.8 billion annually, which stresses the need for alternative therapy.

Summary

Gut commensal bacteria are required for interleukin 25 (IL-25) production by the intestinal epithelium. Disruption of the normal intestinal microbiota by antibiotic treatment renders mice susceptible to *C. difficile* and reduces IL-25 levels, which are further reduced by *C. difficile* infection (CDI). We have discovered that restoration of IL-25 (by administration of IL-25 intraperitoneally) in antibiotic-treated mice prevents lethal CDI. We have also discovered that these observations in the mouse model of CDI are of relevance to humans, as patients with CDI have diminished gut IL-25.

It is disclosed herein that IL-25 is the first component of the host immune response identified to be both dependent on the microbiota and protective against CDI. IL-25 production is reduced by the microbiota and further reduced during CDI. Restoration of IL-25 protects mice from CDI-associated mortality. IL-25 reduces mortality during CDI in an eosinophil dependent mechanism. IL-25 protection is lost when eosinophils are depleted, that is, the presence of eosinophils is required for IL-25 to be effective. Eosinophils are capable of reducing epithelial disruption at the intestinal barrier. Additionally, the levels of eosinophils and IL-25 are useful for determining the type of treatment that will be effective for a subject. Therefore, the present invention allows for the detection, diagnosis, and treatment CDI subjects based on the levels of IL-25 or the levels of eosinophils in an infected subject.

EXAMPLE 2

The following experiments will further define the role and relationships regulating IL-25, eosinophils, the type of bacteria present, and the prevention, treatment and diagnosis of CDI.

Our hypothesis that IL-25 and intestinal eosinophils are protective in CDI is unanticipated and is an unexpected discovery in the field of CDI research. In fact a protective role of eosinophils in almost unprecedented in the field of bacteriology (6). IL-25 promoted gut eosinophils are the major source of IL-4 in our model of CDI, and could be postulated to promote tissue repair via alternatively activated macrophages, or additionally directly through antibacterial properties. Our hypothesis is also well supported by our preliminary data that IL-25 is suppressed in humans with CDI colitis, and that in mice IL-25 protects from death due to CDI and induces eosinophils and finally that IL-25 protection is abrogated by eosinophil depletion. Finally the work is innovative for its translational potential to lead to new therapies, with every Aim having both murine and human studies, and including an in depth analysis of the impact of fecal transplantation in humans on the innate immune response.

We will determine the role of normal components of the gut microbiome in induction of IL-25 to protect from *C. difficile* colitis (CDI). It is disclosed herein that:

IL-25 in the intestinal epithelium is suppressed by antibiotics and by CDI in mice and humans; and that IL-25 rescues mice from death due to *C. difficile* colitis by inducing gut eosinophilia.

Fecal transplantation is an effective treatment to prevent *C. difficile* relapse, but has safety concerns. Next-generation probiotics made with defined bacteria will likely replace fecal transplants, but first we need a better understanding of how commensal bacteria protect the host from *C. difficile*.

Gut commensal bacteria are required for interleukin 25 (IL-25) production by the intestinal epithelium. Disruption of the normal intestinal microbiota by antibiotic treatment renders mice susceptible to *C. difficile* and reduces IL-25 levels, which are further reduced by *C. difficile* infection (CDI). We have demonstrated herein that restoration of IL-25 (by administration of IL-25 intraperitoneally) in antibiotic-treated mice prevents lethal CDI. We have also demonstrated herein that these observations in the mouse model of CDI are of relevance to humans, as patients with CDI have diminished gut IL-25. Here we propose to delineate the mechanism by which IL-25 is induced by specific gut microbiota bacteria and their metabolic products and conversely inhibited by antibiotics and by CDI. We hypothesize that innate protection from CDI is mediated by gut microbiota induced intestinal epithelial cell production of IL-25. We further hypothesize that dysbiosis induced by antibiotics and by CDI inhibits IL-25, rendering mice susceptible. In this example describing a series of three sets of experiments, we will define IL-25 regulation in a healthy host (Study the suppression of IL-25 by antibiotic-induced changes in commensal bacteria), test whether IL-25 inducing bacteria can prevent CDI severity (Test the probiotic potential of IL-25 inducing bacteria to prevent CDI), and evaluate if the mechanism of fecal transplant-mediated protection from CDI is via restoration of IL-25 production (Does fecal transplantation act to prevent CDI via IL-25).

In summary, it will be paradigm shifting for the CDI, mucosal immunology, and bacteriology if as expected IL-25-induced eosinophils are demonstrated to protect from this enteric bacterial infection. Clinically it has the potential to modify current treatment of CDI colitis through probiotic therapy targeted to the bacterial species that induce a protective host innate immune response.

Study the suppression of IL-25 by antibiotic-induced chances in commensal bacteria. Components of the normal intestinal microbiome induce intestinal epithelial IL-25 production. We hypothesize that a specific bacterium or subset of bacteria from the gut microbiome are responsible for IL-25 production by intestinal epithelial cells. We will test this hypothesis by characterizing the gut microbiome and metabolome of (A) untreated C57Bl/6 mice; (B) mice treated with metronidazole (known to increase IL-25 production); and (C) clindamycin-treated (decreased IL-25 production) to identify commensal bacteria and their metabolic products that correlate with IL-25 production. Successful completion of this study will identify specific bacteria or metabolic products associated with increased IL-25 production.

The microbiota composition from the cecal contents from groups A-C will be characterized by bacterial 16S rDNA V4 hypervariable region sequencing. The resulting sequences will be assigned to operational taxonomic units (OTUs) sharing ≥97% nucleotide sequence identity (a 97%-identity OTU is commonly construed as representing a species-level taxon). OUT assignment will use QIIME (v 1.5.0) and be matched to entries in the Greengenes reference database (version 4 Feb. 2011). IL-25 inducing bacterial taxa will be identified by a Random Forests regression of their relative abundances in cecal samples. For this analysis, cecal samples will be snap frozen at −20° C. at the time of collection and subsequently stored at −80° C. before extraction of DNA. DNA will be isolated by bead-beating in phenol and chloroform, purified on a QIAquick column and DNA content quantified. The DNA will be PCR amplified using primers directed at variable region 4 (V4) of bacterial 16S rRNA genes. All reads will be overlapped to 253-nucleotide fragments spanning the entire V4 amplicon as previously published. The goal will be to identify bacterial species associated with increased IL-25 production.

Untargeted metabolome analysis by LC-MS at the University of Virginia core lab will be done using established protocols. Deproteinated and dephospholipidated plasma and fecal samples will be analyzed by LC-MS using four different chromatography/ionization procedures: HILIC chromatography in the positive and negative ion mode and reverse phase chromatography in the positive and negative mode. We expect to obtain a relatively comprehensive metabolite profile (~1000 metabolites) of the plasma. This analysis will focus on relatively polar compounds including amino acids, nucleotides, polyamines, sugars and intermediary metabolites and therefore will not include most lipids. Appropriate QC analysis will be included and the results will be screened to ensure data reproducibility.

The log-transformed m/z peak values obtained from the MS will be subjected to multivariate statistical analysis (PCA and OPLS-DA) to identify peaks that significantly vary in the different groups of samples. Tools like S-plot will be used for visualization and interpretation of chemometric data. Metabolites corresponding to the different peaks will be identified using comprehensive reference metabolite MS spectra libraries including online human metabolome databases. The end result is expected to be identification of potentially significant metabolites that correlate with increased IL-25 production.

These studies describing the changes in composition of the gut microbiome and its metabolic products can then be tested in the murine model through the fecal transplantation studies outlined below.

Test the probiotic potential of IL-25 inducing bacteria to prevent CDI. The ability of probiotics to prevent CDI severity is currently under investigation. We have identified IL-25 as a microbiota-dependent immune modulator effective at reducing CDI associated mortality and morbidity.

We hypothesize that reconstitution with bacteria responsible for IL-25 induction after antibiotic treatment but before *C. difficile* infection will reduce disease severity. We will test this hypothesis by gavaging antibiotic treated mice with (a) stool from metronidazole or clindamycin treated mice, (b) species identified in the studies described above; and (c) with defined bacterial species identified by us or our collaborators.

Does fecal transplantation act to prevent CDI via IL-25? Reconstituting the enteric microbiome through fecal transplantation may restore IL-25 stimulating bacterial species lost during antibiotic treatments. Because exogenous IL-25 protects the host from *C. difficile*, we hypothesize that the re-introduction of IL-25 stimulating bacteria is required for host protection from *C. difficile* following fecal transplantation.

Fecal transplantation is being increasingly utilized for relapses of CDI (2). This treatment is effective in up to 80% of cases in preventing further relapses; however, it is of unknown effectiveness for primary CDI. Disadvantages of fecal transplants include administration by endoscopy, which is an invasive procedure with attendant risks, the potential for transmission of infectious organisms in stool, and possible long-term risks from alteration of the microbiota. Next generation probiotics aimed at replacing FMT are under development (examples include *Clostridium scindens*, non-toxigenic *C. difficile* and *Akkeramansia mucinophila* (3,4) but are of unknown effectiveness for treatment or prevention of primary infection.

A major mechanism by which fecal transplantation and next generation probiotics likely act is via the innate mucosal immune system (see below). We propose that IL-25 production by the intestinal epithelium is a mechanism by which the normal microbiome protects from CDI, and that therefore IL-25 will be a surrogate marker of probiotic-mediated protection. This research proposal additionally may offer advantages to currently inadequate therapy by identifying protective mechanisms downstream of the microbiota, ultimately complementing or supplanting fecal transplants.

Our goal to treat CDI via the innate immune system is biologically plausible. Early inflammation appears to contribute to CDI severity. A hallmark of *C. difficile* infection is trafficking of neutrophils to the site of barrier disruption. Leukocytosis correlated with increased disease severity and a poor patient prognosis. In adults and children, higher levels of the intestinal epithelial chemokines CXCL5 and IL-8 were associated with a slower recovery, whereas the amount of *C. difficile* bacteria in the gut was not. Supporting the potential for innate immune responses to exacerbate CDI is our discovery that IL-23 signaling is up-regulated in humans with CDI and in mice causes death without changing bacterial burden. Finally consistent with our hypothesis that eosinophils are protective from CDI colitis, in humans a low peripheral eosinophil count was a risk factor in for death or persistent diarrhea (5)

In summary, the significance of the proposed research is that it promises to deliver innovative therapeutic approaches for the most common cause of death due to gastroenteritis. Therapy based on IL-25 induction of protective gut eosinophils could be of benefit for both prevention and treatment of CDI colitis.

We will test this hypothesis by: (a) using a fecal gavage strategy to reconstitute a dysbiotic microbiome with the microbiome from antibiotic-untreated control mice; and (b) with defined bacterial species identified by our collaborators and/or identified in experiments outlined above. (c) In humans we will investigate if fecal microbiota transplantation (FMT) restores colonic IL-25 and eosinophil numbers.

In humans, we will investigate if fecal microbiota transplantation (FMT) restores colonic IL-25 and eosinophil numbers. FMT should have a restorative effect.

Co-housing mice to reconstitute a dysbiotic microbiome with that from control mice. If dysbiosis is contributing to IL-25 suppression then IL-25 levels should be restored by FMT using stool from untreated mice (Table 1).

FMT using defined bacterial species identified by our colleagues at Seres Therapeutics and/or identified as outlined above. These studies will be done to identify and use bacteria most appropriated for transplantation.

Test in humans undergoing successful FMT if restoration of colonic IL-25 and eosinophils is observed. Colonic biopsy samples will be obtained from 10 adult patients receiving fecal transplant for relapsing *C. difficile* infection. Samples will be collected at the time of fecal transplant and again 60 (+/-10) days later. This will be performed in a similar manner to our work with amebic colitis where colon biopsy samples were taken during acute disease and later at convalescence for RNA and immunohistochemistry (22).

All biopsies will be obtained from patients seen in the Complicated *C. difficile* Clinic at the University of Virginia. This Clinic performs approximately 50 fecal microbiota transplants (FMT) each year. The success rate for FMT for relapsing *C. difficile* is greater than 90% at this Clinic based on the first 60 patients. Colonoscopy is used to instill the fecal transplant, so patients will require only a follow-up flexible sigmoidoscopy as a research protocol, as well as collection of additional biopsies beyond what is required for the clinical care of the patient. The protocol will be reviewed and approved by the IRB of the University of Virginia and informed consent obtained with the subjects paid a small honorarium for their participation.

Biopsies will be obtained from involved areas of the sigmoid colon in subjects at the time of fecal transplantation. Follow-up biopsies will be obtained from the sigmoid colon during convalescence 60 days after fecal transplant. 8 biopsies will be taken for research purposes at each colonoscopy, and used for: (a) cytokines and chemokines—1 biopsy; (b) gene expression analysis—1 biopsy (also processed for DNA for 16 s rDNA sequencing; (c) immunohistochemistry—2 biopsies; and (d) high dimensional flow-cytometry (single-cell atomic mass spectrometry, CyTOF)—4 biopsies.

Biopsy specimens for cytokines and chemokines will be homogenized in HBSS containing Triton X-100 and HALT protease inhibitor cocktail (Pierce) and analyzed with a luminex panel including IL-25, IL-4 and IL-1b). (b) for gene expression and 16s rDNA sequencing one biopsy will be placed in RNA later (Qiagen, CA) and stored at −80° C. until isolation of RNA for Affymetrix microarray and RT-qPCR and DNA for 16s rDNA microbiota characterization. (c) Biopsy samples for histopathology will be collected in Histocon (Histolab, Gutenberg Sweden). (d) Biopsy samples for immunohistochemistry will be snap frozen in liquid nitrogen for immunohistochemical stain for IL-25 and IL-4 and eosinophils. (e) Four biopsy samples per colonoscopy will be analyzed by CyTOF. These samples will undergo tissue disruption and cell isolation, followed by cryopreservation for CyTOF (23). CyTOF will be performed not only to quantify eosinophils that are expected after successful fecal transplant, but also in a hypothesis-generating fashion to deeply characterize the phenotypes of intestinal immune cells pre- and post-fecal transplantation. This analysis will allow us to identify cellular correlates of relapsing CDI and how these correlates change or improve with fecal transplantation, and should help lead us to a more mechanistic understanding of this intervention. We will use an available CyTOF panel. The primary hypothesis to be tested is that successful fecal transplantation will restore IL-25, IL-4 and eosinophils to the colon. Statistical analyses of the biopsy data will include univariate analysis at a 20% false discovery rate for the ratio of the biomarker pre- and post-fecal transplant (using the patient as their own control) as well as multiple regression analyses to identify correlates of intestinal health. The number of patients required to adequately power this analysis is derived from our prior work for another infectious colitis due to *Entamoeba histolytica*. In that study, eight patients were sufficient to identify statistically significant changes in gene expression, again using the patients as their own controls (i.e. data will be primarily analyzed as the ratio of the biomarker pre- and post-transplant in the same patient).

Summary of Analyses for Colon Biopsies Pre- and Post Fecal Transplant:
- cytokine and chemokine analysis, focusing on IL-25 and IL-4
- mRNA analysis by Affymetrix array for signatures of a Th2-type immune response
- IHC for IL-25 and IL-4
- CyTOF for eosinophils and deep immunophenotyping
- 16s rDNA sequencing of colonic luminal contents and of one biopsy (to identify luminal and epithelial-adherent microbiota)
- plasma for metabolomics including short chain fatty acids, bile acids, phosphatidylcholine metabolites and trimethylamine.

TABLE 1

Fecal microbiota transplantation (FMT) in mice to test the role of dysbiosis in IL-25 suppression.

| Recipient Mouse: | Donor Stool: | Expected IL-25 levels if dysbiosis blocks IL-25: |
|---|---|---|
| Normal (no antibiotics, no CDI) | (—) | High (↑↑↑) |
| | Normal stool | High (↑↑↑) |
| | Clindamycin treated stool | Low to medium (↑ to ↑↑) |
| | Metronidazole treated stool | High (↑↑↑) |
| Clindamycin-treated | (—) | Low (↓) |
| | Normal stool | High (↑↑↑) |
| | Clindamycin treated stool | Low (↓) |
| | Metronidazole treated stool | High (↑↑↑) |
| Clindamycin treated and *C. difficile* colitis | (—) | Very low (—) |
| | Normal stool | High (↑↑↑) |
| | Clindamycin treated stool | Very low (—) |
| | Metronidazole treated stool | High (↑↑↑) |

TABLE 2

Table 2. Proposed CyTOF Ab staining panel.

| Isotope Cd Qdot | Marker CD3 qdot |
|---|---|
| 103 | CD45 |
| 115 | Live/dead |
| 139 | IFN-γ |
| 141 | TNF-α |
| 142 | MIP-1β |
| 143 | Perforin |
| 144 | CD45RO |
| 145 | GM-CSF |
| 146 | CD8α |
| 147 | CD40L |
| 148 | Granzyme B |
| 149 | CD4 |
| 150 | IL-10 (bio-SAv) |
| 151 | CD20 |
| 152 | HLA-DR |
| 153 | CD107a/b |
| 154 | CD27 |
| 155* | CD13 |
| 156 | IL-22 |
| 157* | CD19 |
| 158 | Integrin αE |
| 159 | CTLA-4 |
| 160 | CD28 |
| 161* | CD8β (a-APC) |
| 162 | IL-4 |
| 163 | CD294 |
| 164 | IL17 |
| 165 | CD138 |
| 166 | IL-2 |
| 167 | Integrin β7 |
| 168 | CD38 |
| 169 | IgA |
| 170 | CD25 |
| 171 | CD127 |
| 172 | Integrin α4 |
| 173* | γδ TCR (a-PE) |
| 174 | CCR9 (a-FITC) |
| 175 | CCR10 |
| 176 | IgD |

All of these markers have now been validated in small intestine tissue and blood samples. In this table, the atomic mass of each isotopic label is listed for each Ab marker.
*Indicates isotopes with up to 2% impurities with +1 AMU isotopes. For some markers, which have not performed well with standard polymer-coupling techniques or are not available in purified format, we are using metal-conjugated secondary antibodies directed against fluorophore-labeled primary antibodies as indicated (e.g., a-APC, etc.) or biotin-streptavidin as indicated for IL-10.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

Example 1—
1. Dubberke, E. R., and Olsen, M. A. (2012). Burden of Clostridium difficile on the Healthcare System. Clin Infect Dis. 55, S88-S92. PMCID: PMC3388018
2. Loo, V. G., Poirier, L., Miller, M. A., Oughton, M., Libman, M. D., Michaud, S., Bourgault, A.-M., Nguyen, T., Frenette, C., Kelly, M., et al. (2005). A Predominantly Clonal Multi-Institutional Outbreak of Clostridium difficile-Associated Diarrhea with High Morbidity and Mortality. New England Journal of Medicine 353, 2442-2449. PMID: 16322602
3. Maroo, S., and Lamont, J. T. (2006). Recurrent Clostridium Difficile. Gastroenterology 130, 1311-1316. PMID: 16618421
4. Rupnik, M., Wilcox, M. H., and Gerding, D. N. (2009). Clostridium difficile infection: new developments in epidemiology and pathogenesis. Nat Rev Micro 7, 526-536. PMID: 19528959
5. Miller, B. A., Chen, L. F., Sexton, D. J., and Anderson, D. J. (2011). Comparison of the Burdens of Hospital-Onset, Healthcare Facility-Associated Clostridium difficile Infection and of Healthcare-Associated Infection due to Methicillin-Resistant Staphylococcus aureus in Community Hospitals. Infection Control and Hospital Epidemiology 32, 387-390. PMID: 21460491
6. Hall A J, Curns A T, McDonald L C, Parashar U D, Lopman B A. The Roles of Clostridium difficile and Norovirus Among Gastroenteritis-Associated Deaths in the United States, 1999-2007. Clin Infect Dis. 2012 July; 55(2): 216-23 PMID: 22491338
7. Bulusu, M., Narayan, S., Shetler, K., and Triadafilopoulos, G. (2000). Leukocytosis as a harbinger and surrogate marker of Clostridium difficile infection in hospitalized patients with diarrhea. Am J Gastroenterol 95, 3137-3141. PMID: 11095331
8. El Feghaly, R. E., Stauber, J. L., Deych, E., Gonzalez, C., Tarr, P. I., and Haslam, D. B. (2013). Markers of intestinal inflammation, not bacterial burden, correlate with clinical outcomes in Clostridium difficile infection. Clin. Infect. Dis. 56, 1713-1721. PMID: 23487367
9. Zaph, C., Du, Y., Saenz, S., Nair, M. et al. (2008). Commensal-dependent expression of IL-25 regulates the IL-23-IL-17 axis in the intestine. The Journal of experimental medicine. 205(10): 2191-98.

Buffie, C., et al., "Precision microbiome reconstitution restores bile acid mediated resistance to Clostridium Difficile", Nature, 2015, V517, pp 205-220.

Lawley, T., et al., "Targeted Restoration of the Intestinal Microbiota with a Simple, Defined Bacteriotherapy Resolves Relapsing Clostridium Difficile Disease in Mice", Plos Pathogens, October 2012, V8, Issue 10, pp 1-14.

Example 2—
1. Lessa, F. C. et al. Burden of Clostridium difficile infection in the United States. N. Engl. J. Med. 372, 825-834 (2015).
2. Brandt, L. J. Fecal Transplantation for the Treatment of Clostridium difficile Infection. Gastroenterol Hepatol (N Y) 8, 191-194 (2012).
3. Buffie, C. G. et al. Precision microbiome reconstitution restores bile acid mediated resistance to Clostridium difficile. Nature 517, 205-208 (2015).
4. Kau, A. L. et al. Functional characterization of IgA-targeted bacterial taxa from undernourished Malawian children that produce diet-dependent enteropathy. Science translational medicine 7, 276ra24-276ra24 (2015).
5. Crook, D. W. et al. Fidaxomicin Versus Vancomycin for Clostridium difficile Infection: Meta-analysis of Pivotal Randomized Controlled Trials. Clinical Infectious Diseases 55, S93-S103 (2012).
6. Linch, S. N. et al. Mouse Eosinophils Possess Potent Antibacterial Properties In Vivo. Infection and Immunity 77, 4976-4982 (2009).
7. Cowardin, C. A. et al. Inflammasome activation contributes to interleukin-23 production in response to Clostridium difficile. MBio 6, (2015).
8. Zaph, C. et al. Commensal-dependent expression of IL-25 regulates the IL-23-IL-17 axis in the intestine. Journal of Experimental Medicine 205, 2191-2198 (2008).
9. Buonomo, E. L. et al. Role of IL-23 signaling in Clostridium difficile Colitis. J Infect Dis. jit277 (2013). doi:10.1093/infdis/jit277
10. Schwan, C. et al. Clostridium difficile toxin CDT induces formation of microtubule-based protrusions and increases adherence of bacteria. PLoS Pathog. 5, e1000626 (2009).
11. Fallani, M. et al. Clostridium difficile and Clostridium perfringens species detected in infant faecal microbiota using 16S rRNA targeted probes. J. Microbiol. Methods 67, 150-161 (2006).
12. Hemmasi, S. et al. Interaction of the Clostridium difficile Binary Toxin CDT and its Host Cell Receptor LSR. J. Biol. Chem. (2015). doi:10.1074/jbc.M115.650523
13. Papatheodorou, P. et al. Lipolysis-stimulated lipoprotein receptor (LSR) is the host receptor for the binary toxin Clostridium difficile transferase (CDT). Proc. Natl. Acad. Sci. U.S.A. 108, 16422-16427 (2011).
14. Feghaly, R. E. E. et al. Markers of Intestinal Inflammation, Not Bacterial Burden, Correlate With Clinical Outcomes in Clostridium difficile Infection. Clin Infect Dis. (2013). doi:10.1093/cid/cit147
15. Archbald-Pannone, L. R., Boone, J. H., Carman, R. J., Lyerly, D. M. & Guerrant, R. L. Clostridium difficile ribotype 027 is most prevalent among inpatients admitted from long-term care facilities. Journal of Hospital Infection 88, 218-221 (2014).
16. Boone, J. H. et al. Ribotype 027 Clostridium difficile infections with measurable stool toxin have increased lactoferrin and are associated with a higher mortality. European Journal of Clinical Microbiology & Infectious Diseases 33, 1045-1051 (2014).
17. Boone, J. H. et al. Elevated lactoferrin is associated with moderate to severe Clostridium difficile disease, stool toxin, and 027 infection. European Journal of Clinical Microbiology & Infectious Diseases 32, 1517-1523 (2013).
18. Zaiss, M. M. et al. IL-1β Suppresses Innate IL-25 and IL-33 Production and Maintains Helminth Chronicity. PLoS Pathog 9, e1003531 (2013).

19. Hasegawa, M. et al. Protective role of commensals against *Clostridium difficile* infection via an IL-1β-mediated positive-feedback loop. *J. Immunol.* 189, 3085-3091 (2012).
20. Yamamoto, M. et al. ASC is essential for LPS-induced activation of procaspase-1 independently of TLR-associated signal adaptor molecules. *Genes Cells* 9, 1055-1067 (2004).
21. Zaki, M. H. et al. The NLRP3 Inflammasome Protects against Loss of Epithelial Integrity and Mortality during Experimental Colitis. *Immunity* 32, 379-391 (2010).
22. Peterson, K. M. et al. The expression of REG 1A and REG 1B is increased during acute amebic colitis. *Parasitol. Int.* 60, 296-300 (2011).
23. Naylor, C. et al. Leptin Receptor Mutation Results in Defective Neutrophil Recruitment to the Colon during *Entamoeba histolytica* Infection. *mBio* 5, e02046-14 (2014).
24. Linch, S. N. et al. Mouse eosinophils possess potent antibacterial properties in vivo. *Infect. Immun.* 77, 4976-4982 (2009).
25. Jacobsen, E. A., Zellner, K. R., Colbert, D., Lee, N. A. & Lee, J. J. Eosinophils Regulate Dendritic Cells and Th2 Pulmonary Immune Responses following Allergen Provocation. *J Immunol* 187, 6059-6068 (2011).
26. Pero, R. S. et al. Gαi2-mediated signaling events in the endothelium are involved in controlling leukocyte extravasation. *PNAS* 104, 4371-4376 (2007).
27. Ohnmacht, C., Pullner, A., Rooijen, N. van & Voehringer, D. Analysis of Eosinophil Turnover In Vivo Reveals Their Active Recruitment to and Prolonged Survival in the Peritoneal Cavity. *J Immunol* 179, 4766-4774 (2007).
28. Walsh, E. R. et al. Strain-specific requirement for eosinophils in the recruitment of T cells to the lung during the development of allergic asthma. *J Exp Med* 205, 1285-1292 (2008).
29. Cormier, S. A. et al. Pivotal Advance: Eosinophil infiltration of solid tumors is an early and persistent inflammatory host response. *J Leukoc Biol* 79, 1131-1139 (2006).
30. Warren, C. A. et al. Amixicile, a Novel Inhibitor of Pyruvate:Ferredoxin Oxidoreductase, Shows Efficacy against *Clostridium difficile* in a Mouse Infection Model. *Antimicrobial Agents and Chemotherapy* 56, 4103-4111 (2012).
31. Isobe, Y., Kato, T. & Arita, M. Emerging Roles of Eosinophils and Eosinophil-Derived Lipid Mediators in the Resolution of Inflammation. *Front Immunol* 3, (2012).
32. Masterson, J. C. et al. Eosinophil-mediated signalling attenuates inflammatory responses in experimental colitis. *Gut* gutjnl-2014-306998 (2014). doi:10.1136/gutjnl-2014-306
33. Pituch, H. et al. Detection of binary-toxin genes (cdtA and cdtB) among *Clostridium difficile* strains isolated from patients with *C. difficile*-associated diarrhoea (CDAD) in Poland. *J. Med. Microbiol.* 54, 143-147 (2005).
34. Subramanian S, Huq S, Yatsunenko T, Haque R, Mahfuz M, Alam M A, Benezra A, DeStefano J, Meier M F, Muegge B D, Barratt M J, VanArendonk L G, Zhang Q, Province M A, Petri W A Jr, Ahmed T, Gordon M. (2014) Persistent gut microbiota immaturity in malnourished Bangladeshi children. Nature 510:417-421. PMCID: PMC4189846
35. Sharon, Gil, et al. "Specialized metabolites from the microbiome in health and disease." *Cell metabolism* 20.5 (2014): 719-730.
36. Yau Y Y[1], Leong R W[2], Shin S[3], Bustamante S[3], Pickford R[3], Hejazi L[3], Campbell B[3], Wasinger V C[3]. Bimodal plasma metabolomics strategy identifies novel inflammatory metabolites in inflammatory bowel diseases. Discov Med. 2014 September; 18(98):113-24.
37. W B Dunn, Broadhurst D, Begley P, Zelena E, Francis-McIntyre S, Anderson N, Brown M, Knowles J D, Halsall A, Haselden J N, Nicholls A W, Wilson I D, Kell D B, Goodacre R & The Human Serum Metabolome (HUSERMET) Consortium. Procedures for large-scale metabolic profiling of serum and plasma using gas chromatography and liquid chromatography coupled to mass spectrometry. Nature Prot. 2011; 6(7):1060-1083.
38. Zhou B, Xiao J F, Tuli L and Ressom H W. LC-MS-based metabolomics. Mol. BioSyst., 2012, 8: 470-481.
39. Tulipani S, Mora-Cubillos X, Jauregui O, Llorach R, Garcia-Fuentes E, Tinahones F J, Andres-Lacueva C. New and vintage solutions to enhance the plasma metabolome coverage by LC-ESI-MS untargeted metabolomics: the not-so-simple process of method performance evaluation. Anal Chem. 2015 Mar. 3; 87(5):2639-47.
40. Buffie, C., et al., "Precision microbiome reconstitution restores bile acid mediated resistance to *Clostridium Difficile*", Nature, 2015, V517, pp 205-220.
41. Lawley, T., et al., "Targeted Restoration of the Intestinal Microbiota with a Simple, Defined Bacteriotherapy Resolves Relapsing *Clostridium Difficile* Disease in Mice", Plos Pathogens, October 2012, V8, Issue 10, pp 1-14.

What is claimed is:

1. A method for treating a *Clostridium difficile* (*C. difficile*) infection in a subject in need thereof, the method comprising administering to the subject a pharmaceutical composition comprising a pharmaceutically-acceptable carrier, an effective amount of IL-25 and optionally an additional therapeutic agent, thereby treating said *C. difficile* infection.

2. The method of claim 1, wherein said IL-25 is recombinant IL-25.

3. The method of claim 1, wherein said method increases survival of said subject.

4. The method of claim 3, wherein said method increases survival of said subject by about 10% to about 68% compared to a subject not receiving said treatment.

5. The method of claim 4, wherein said method increases survival of said subject by about 45% compared to a subject not receiving said treatment.

6. The method of claim 1, wherein said method stimulates eosinophil recruitment to lamina propria of the intestine.

7. The method of claim 6, wherein said method induces IL-4 synthesis in said eosinophils.

8. The method of claim 1, wherein said method stimulates eosinophil recruitment or levels in the colon.

9. The method of claim 1, wherein said method stimulates mucin expression.

10. The method of claim 9, wherein said mucin expression increases in lamina propria.

11. The method of claim 1, wherein said method stimulates IL-10 expression.

12. The method of claim 1, wherein said subject is susceptible to a *C. difficile* infection.

13. The method of claim 12, wherein said subject is pretreated to reduce the severity of a *C. difficile* infection if said infection occurs in the subject.

14. The method of claim 13, wherein when said subject is pretreated and said subject becomes infected with *C. difficile*, said method reduces morbidity and mortality.

15. The method of claim 13, wherein said method increases survival of said subject by about 10% to about 68% compared to a subject not receiving said treatment.

16. The method of claim 15, wherein said method increases survival of said subject by about 45% compared to a subject not receiving said treatment.

17. The method of claim 1, wherein said method inhibits epithelial disruption by *C. difficile* in the colon.

18. The method of claim 17, wherein said method does not alter the *C. difficile* burden.

19. The method of claim 17, wherein said method does not stimulate neutrophil recruitment.

20. The method of claim 1, wherein said method decreases IL-23 expression or levels.

21. The method of claim 1, wherein said IL 25 is administered at a dose of about 1.0 µg IL-25/kilogram (kg) body weight to about 2500 µg IL-25/kg body weight.

22. The method of claim 21, wherein said IL 25 is administered at a dose of about 10 µg IL-25/kg body weight to about 1500 µg IL-25/kg body weight.

23. The method of claim 22, wherein said IL 25 is administered at a dose of about 25 µg IL-25/kg body weight to about 500 µg IL-25/kg body weight.

24. The method of claim 1, wherein said IL 25 is administered at a dose of about 25 µg IL-25/kg body or about 62.5 µg IL-25/kg body weight.

25. The method of claim 1, wherein said method reduces recurrent *C. difficile* infection in a subject susceptible to recurrent infection.

26. The method of claim 1, wherein said method reduces *C. difficile* infection in a subject susceptible to said infection following prior antibiotic therapy.

27. The method of claim 1, wherein said method reduces *C. difficile* infection in a subject susceptible to said infection following H-2 blocker therapy or stem cell transplant.

28. The method of claim 1, wherein said method reduces *C. difficile* associated colitis.

29. The method of claim 28, wherein said subject received prior antibiotic therapy.

30. The method of claim 29, wherein said subject is infected with *C. difficile*.

31. A method for treating a *C. difficile* infection in a subject in need thereof, the method comprising administering to the subject a pharmaceutical composition comprising a pharmaceutically-acceptable carrier, an effective amount of a stimulator of eosinophil recruitment in the gut or an effective amount of an inducer of IL-4 production by eosinophils in the intestine, wherein the stimulator of eosinophil recruitment in the gut or the inducer of IL-4 production is IL-25 and optionally an additionally therapeutic agent, thereby treating said *C. difficile* infection.

* * * * *